(12) United States Patent
Zhou et al.

(10) Patent No.: US 8,777,413 B2
(45) Date of Patent: Jul. 15, 2014

(54) OPHTHALMIC WAVEFRONT SENSOR OPERATING IN PARALLEL SAMPLING AND LOCK-IN DETECTION MODE

(75) Inventors: Yan Zhou, Pleasanton, CA (US); William Shea, Pleasanton, CA (US); Phil Baker, Walnut Grove, CA (US)

(73) Assignee: Clarity Medical Systems, Inc., Pleasanton, CA (US)

( * ) Notice: Subject to any disclaimer, the term of this patent is extended or adjusted under 35 U.S.C. 154(b) by 23 days.

(21) Appl. No.: 13/459,914

(22) Filed: Apr. 30, 2012

(65) Prior Publication Data

US 2012/0268717 A1    Oct. 25, 2012

Related U.S. Application Data

(60) Continuation-in-part of application No. 13/198,442, filed on Aug. 4, 2011, now Pat. No. 8,356,900, which is a continuation-in-part of application No. 12/790,301, filed on May 28, 2010, now Pat. No. 8,579,437, which is a division of application No. 11/761,890, filed on Jun. 12, 2007, now Pat. No. 7,815,310, which is a continuation-in-part of application No. 11/335,980, filed on Jan. 20, 2006, now Pat. No. 7,445,335, application No. 13/459,914, which is a continuation-in-part of application No. 13/154,293, filed on Jun. 6, 2011, now Pat. No. 8,506,083.

(51) Int. Cl.
*A61B 3/14* (2006.01)
*A61B 3/10* (2006.01)
*A61B 3/103* (2006.01)
*A61B 3/12* (2006.01)

(52) U.S. Cl.
CPC ............... *A61B 3/1015* (2013.01); *A61B 3/103* (2013.01); *A61B 3/12* (2013.01)
USPC .................... 351/210; 351/206; 351/221

(58) Field of Classification Search
CPC ....... A61B 3/1015; A61B 3/103; A61B 3/0075
USPC ......... 351/205, 210, 211, 212, 214, 221, 246, 351/247
See application file for complete search history.

(56) References Cited

U.S. PATENT DOCUMENTS 4,141,652 A    2/1979 Feinleib
5,164,578 A    11/1992 Witthoft
(Continued)

FOREIGN PATENT DOCUMENTS

EP    1 618 838 A1    1/2006
EP    2 103 249 A1    9/2009
(Continued)

OTHER PUBLICATIONS

Dave, T., "Wavefront aberrometry Part 1: Current Theories and Concepts", Optometry Today, Nov. 19, 2004, pp. 41-45.
(Continued)

*Primary Examiner* — Huy K Mai
(74) *Attorney, Agent, or Firm* — Kilpatrick Townsend & Stockton LLP

(57) ABSTRACT

One embodiment of the present invention is an ophthalmic wavefront sensor for use with an ophthalmic microscope to provide continuous measurements of the refractive state of an eye. The wavefront sensor operates in both parallel sampling and lock-in detection mode by synchronizing the pulsing of the light source with a multiple number of position sensing devices/detectors used for detecting the centroid position of the sampled sub-wavefronts. Other embodiments include a beam scanner to sample selected portions of the wavefront and a live image sensor and a tracking deflector.

41 Claims, 12 Drawing Sheets

(56) References Cited

U.S. PATENT DOCUMENTS

| | | |
|---|---|---|
| 5,568,208 A | 10/1996 | Van de Velde |
| 5,777,719 A | 7/1998 | Williams |
| 6,199,986 B1 | 3/2001 | Williams |
| 6,376,819 B1 | 4/2002 | Neal |
| 6,409,345 B1 | 6/2002 | Molebny |
| 6,530,917 B1 | 3/2003 | Seiler |
| 6,561,648 B2 | 5/2003 | Thomas |
| 6,572,230 B2 | 6/2003 | Levine |
| 6,578,963 B2 | 6/2003 | Pettit |
| 6,595,642 B2 | 7/2003 | Wirth |
| 6,685,317 B2 | 2/2004 | Su et al. |
| 6,685,319 B2 | 2/2004 | Watson |
| 6,709,108 B2 | 3/2004 | Levine et al. |
| 6,736,510 B1 | 5/2004 | Van Heugten |
| 6,781,681 B2 | 8/2004 | Horwitz |
| 6,784,408 B1 | 8/2004 | Cheung |
| 6,791,696 B1 | 9/2004 | Fantone et al. |
| 6,793,654 B2 | 9/2004 | Lemberg |
| 6,827,444 B2 | 12/2004 | Williams et al. |
| 6,880,933 B2 | 4/2005 | Davis |
| 6,890,076 B2 | 5/2005 | Roorda |
| 6,910,770 B2 | 6/2005 | Campbell |
| 6,932,475 B2 | 8/2005 | Molebny |
| 6,964,480 B2 | 11/2005 | Levine |
| 7,057,806 B2 | 6/2006 | Atkinson |
| 7,284,862 B1 | 10/2007 | Lai |
| 7,414,712 B2 | 8/2008 | Yoon |
| 7,445,335 B2 | 11/2008 | Su et al. |
| 7,554,672 B2 | 6/2009 | Greenaway |
| 7,665,846 B2 | 2/2010 | Campin et al. |
| 7,771,048 B2 | 8/2010 | Dai et al. |
| 7,815,310 B2 | 10/2010 | Su et al. |
| 7,883,505 B2 | 2/2011 | Van Heugten |
| 7,988,291 B2 | 8/2011 | Van Heugten |
| 8,002,410 B2 | 8/2011 | Shea |
| 8,100,530 B2 | 1/2012 | Zhou |
| 8,454,162 B2 | 6/2013 | Zhou et al. |
| 8,579,437 B2 | 11/2013 | Su et al. |
| 8,591,027 B2 | 11/2013 | Su et al. |
| 2001/0019361 A1 | 9/2001 | Savoye |
| 2002/0159030 A1 | 10/2002 | Frey |
| 2002/0169441 A1 | 11/2002 | Lemberg |
| 2003/0038921 A1 | 2/2003 | Neal et al. |
| 2003/0053031 A1 | 3/2003 | Wirth |
| 2003/0063257 A1 | 4/2003 | Molebny |
| 2003/0086063 A1* | 5/2003 | Williams et al. ............... 351/221 |
| 2003/0174281 A1 | 9/2003 | Herekar et al. |
| 2003/0223037 A1 | 12/2003 | Chernyak |
| 2004/0004696 A1 | 1/2004 | Davis et al. |
| 2004/0008321 A1 | 1/2004 | Saigussa et al. |
| 2004/0156015 A1 | 8/2004 | Campbell |
| 2004/0239876 A1 | 12/2004 | Levine |
| 2005/0007551 A1 | 1/2005 | Wakil et al. |
| 2005/0094100 A1 | 5/2005 | Ross et al. |
| 2005/0134851 A1 | 6/2005 | Murphy |
| 2006/0077347 A1 | 4/2006 | Liang |
| 2006/0203196 A1 | 9/2006 | Van Heugten |
| 2007/0252951 A1 | 11/2007 | Hammer et al. |
| 2007/0291230 A1 | 12/2007 | Yamaguchi et al. |
| 2008/0018855 A1 | 1/2008 | Larichev et al. |
| 2008/0284979 A1 | 11/2008 | Yee et al. |
| 2009/0185132 A1 | 7/2009 | Raymond |
| 2010/0110379 A1 | 5/2010 | Zhou |
| 2010/0165290 A1 | 7/2010 | Shea |
| 2010/0208203 A1 | 8/2010 | Sarver |
| 2010/0231858 A1 | 9/2010 | Su et al. |
| 2011/0164220 A1 | 7/2011 | Su |
| 2012/0026466 A1 | 2/2012 | Zhou |
| 2012/0188506 A1* | 7/2012 | Zhou et al. .................... 351/205 |
| 2012/0238904 A1* | 9/2012 | Manns et al. ................. 600/558 |
| 2012/0268717 A1 | 10/2012 | Zhou |
| 2013/0265541 A1 | 10/2013 | Zhou |

FOREIGN PATENT DOCUMENTS

| | | |
|---|---|---|
| GB | 2 399 627 A | 9/2004 |
| WO | 03/020167 A2 | 3/2003 |
| WO | 2004/021875 A1 | 3/2004 |
| WO | 2007/087058 A1 | 8/2007 |

OTHER PUBLICATIONS

Ginis, H.S. et al., Variability of wavefront aberration measurements in small pupil sizes using a clinical Shack-Hartmann aberrometer, BMC Ophthalmology, Feb. 11, 2004, 4:1 copyright 2004 Ginis et al.

Liang, J. et al., Objective measurements of wave aberrations of the human eye with the use of a Hartmann-Shack wavefront sensor, J. Opt. Soc. Am. A., vol. 11, No. 7, Jul. 1994, pp. 1949-1957, copyright 1994 Optical Society of America.

Goodman, J., "Introduction to Fourier Optics, Second Edition," The McGraw-Hill Companies, Inc., 1998, pp. 232-233, 273-274.

Wei, Xin et al., "Design and validation of a scanning Shack-Hartmann aberrometer for measurements of the eye over a wide field of view," Optics Express, OSA, Jan. 18, 2010, vol. 18, No. 2, pp. 1-10.

Widiker, J. et al., "High speed Shack-Hartmann wavefront sensor design with commercial off-the-shelf optics," Applied Optics, vol. 45, Jan. 2006, pp. 393-395.

Zawadzki, Robert J. et al., "Challenges and possibilities for developing adaptive optics—ultra-high resolution optical coherence tomography for clinical in vivo retinal imaging," Proc of SPIE, vol. 7139, Dec. 30, 2008, pp. 71390X-1 to 71390X-9.

International Search Report issued in connection with corresponding International Application No. PCT/US2013/036850, mailed Jul. 22, 2013, 2 pages.

* cited by examiner

OPHTHALMIC WAVEFRONT SENSOR OPERATING IN PARALLEL SAMPLING AND LOCK-IN DETECTION MODE

RELATED APPLICATIONS

This application is a continuation-in-part of application U.S. patent application Ser. No. 13/198,442 entitled A Large Diopter Range Real Time Wavefront Sensor, filed Aug. 4, 2011, which is a continuation-in-part of application Ser. No. 12/790,301 entitled Adaptive Sequential Wavefront Sensor With Programmed Control, filed May 28, 2010, which is a division of application Ser. No. 11/761,890 entitled Adaptive Sequential Wavefront Sensor and its Applications, filed Jun. 12, 2007, now U.S. Pat. No. 7,815,310 issued Oct. 19, 2010, which is a continuation-in-part of application Ser. No. 11/335,980 entitled Sequential Wavefront Sensor, filed Jan. 20, 2006, now U.S. Pat. No. 7,445,335 issued Nov. 4, 2008 and this application is also a continuation-in-part of application Ser. No. 13/154,293 entitled A Compact Wavefront Sensor Module and Its Attachment to or Integration with an Ophthalmic Instrument, filed Jun. 6, 2011 all of which are incorporated by reference for all purposes.

TECHNICAL FIELD OF THE INVENTION

One or more embodiments of the present invention relate generally to wavefront sensors for determining the refractive state and wavefront aberrations of an eye. In particular, the invention is an apparatus for determining the refractive state and wavefront aberrations of an eye during ophthalmic surgery.

BACKGROUND OF THE INVENTION

Wavefront sensors are devices used to measure the shape of a wavefront of light (see, for example, U.S. Pat. No. 4,141, 652 and U.S. Pat. No. 5,164,578). In most cases, a wavefront sensor measures the departure of a wavefront from a reference wavefront or an ideal wavefront such as a plane wavefront. A wavefront sensor can be used for measuring both low order and high order aberrations of various optical imaging systems such as the human eye (see for example, U.S. Pat. No. 6,595,642; J. Liang, et al. (1994) "Objective measurement of the wave aberrations of the human eye with the use of a Hartmann-Shack wave-front sensor," J. Opt. Soc. Am. A 11, 1949-1957; T. Dave (2004) "*Wavefront aberrometry Part 1: Current theories and concepts*" Optometry Today, 2004 Nov. 19, page 41-45). Furthermore, a wavefront sensor can also be used in adaptive optics in which the distorted wavefront can be measured and compensated in real time, using, for example, an optical wavefront compensation device such as a deformable mirror (see for example U.S. Pat. No. 6,890,076, U.S. Pat. No. 6,910,770 and U.S. Pat. No. 6,964,480). As a result of such compensation, a sharp image can be obtained (see for example U.S. Pat. No. 5,777,719).

The term "phakic eye" refers to an eye including its natural lens, the term "aphakic eye" refers to an eye with its natural lens removed and the term "pseudo-phakic eye" refers to an eye with an artificial lens implanted. Currently, most wavefront sensors for measuring the aberration of a human eye are designed to only cover a limited diopter range of about –20D to +20D for a phakic or pseudo-phakic eye. In addition, they are also designed to operate in a relatively dark environment when the eye wavefront is to be measured.

During ophthalmic surgeries that affect refraction, it is desirable to know the refractive state of the eye as the surgery is on-going so that a continuous feedback can be provided to the surgeon (see for example, U.S. Pat. No. 6,793,654, U.S. Pat. No. 7,883,505 and U.S. Pat. No. 7,988,291). This is especially the case in cataract surgery in which the natural lens of the eye is replaced by a synthetic lens. In such a case, the surgeon prefers to know the refractive state of the eye in the phakic, aphakic and pseudo-phakic stage in order to select a synthetic lens, confirm if its refractive power is correct after the natural lens is removed, and also to confirm emmetropia or other intended diopter values after the synthetic lens is implanted. Therefore, there is a need for a wavefront sensor to cover a larger diopter measurement range and also to allow the surgeon to measure the refractive state of the eye, with a specified degree of precision, at not only the phakic and pseudo-phakic state but also at the aphakic state.

Also during ophthalmic surgery, the eye is illuminated with unpolarized broadband (white) light from the surgical microscope so the surgeon can see the patient eye through the microscope. This illuminating light is also directed into the eye of the patient, scattered from the retina, and returned to the surgical microscope. A wavefront sensor coupled to the surgical microscope receives both its intended returned wavefront measurement light and the broadband illumination from the surgical microscope. The microscope illumination light source is generally not designed to produce a sufficiently-small effective source of light at the retina that is required to generate a wavefront that reveals the patient's refractive state. Because of this, any illumination light from the surgical microscope that is accepted by the wavefront sensor can lead to incorrect information about the patient's refractive state. Therefore, there is also a need for an ophthalmic wavefront sensor that is immune to influence of the illumination light from a surgical microscope.

Commercially available wavefront sensors for cataract surgery, such as the ORange intraoperative wavefront aberrometer from WaveTec Vision (see for example, U.S. Pat. No. 6,736,510), do not provide continuous feedback, are limited in refractive diopter range coverage and also are not immune to interference from the illumination light of the surgical microscope. In fact, in order to get a sufficiently precise and accurate refraction measurement using the ORange wavefront sensor, the surgeon has to pause the surgical procedure, turn off the illumination light of the surgical microscope, and has to capture multiple frames of data, which leads to additional time up to several minutes added to the cataract refractive surgery time.

SUMMARY OF THE INVENTION

One embodiment of the invention concerns an ophthalmic wavefront sensor comprising a light source configured to receive a reference signal oscillating/pulsing at a reference frequency and to generate a beam of light formed by pulses of light at the reference frequency, a beam directing element configured to launch the beam of light from the light source into a patient eye and where a portion of the beam of light returned from the patient eye forms an object wavefront in the form of light pulses at the reference frequency, an optical wavefront relay system, configured to relay an object wavefront from an object plane located at the anterior portion of a patient eye to a wavefront image plane along a beam path that can guide an incident wavefront relay beam having a large diopter range at the object plane to the wavefront image plane, an array of high frequency response position sensing devices with each position sensing device configured to detect the amount of deflection of an image spot centroid from a reference position and to output a measurement signal indicating the amount of deflection, an array of sub-wavefront sampling elements, disposed before the array of high frequency response position sensing devices and substantially at the wavefront image plane, with each sampling element in the array of sub-wavefront sampling elements configured to sample a sub-wavefront of the relayed wavefront and to focus a sampled sub-wavefront onto a corresponding high frequency response position sensing device in the array of high frequency response position sensing devices, where the sub-wavefront sampling elements are physically spaced from each other in such a way that each sampled sub-wavefront of a high diopter range object wavefront is focused only on the corresponding high frequency response position sensing device corresponding to the sub-wavefront sampling element and an electronic frequency-sensitive detection system coupled to receive the reference signal and the measurement signal, with the electronic frequency-sensitive detection system configured to indicate only the magnitude of a frequency component of the measurement signal at about the reference frequency so that all noise signals, such as 1/f noise, at frequencies different from the reference frequency can be substantially suppressed.

One feature is the use of two cascaded wavefront relays with the second relay having a Fourier transform plane where the wavefront relay beam is made to reside within a certain space volume when the wavefront from the eye changes over a large diopter range. A beam scanner/deflector is disposed at the Fourier transform plane of the second relay to angularly scan the beam so that the relayed wavefront at the final wavefront image plane can be transversely shifted relative to an array of a number of sub-wavefront sampling elements. A corresponding number of PSDs are disposed behind the wavefront sampling elements to operate in lock-in detection mode in synchronization with a pulsed light source that generate the wavefront from the eye. With transverse wavefront shifting, any portion of the relayed wavefront can be sampled and the spatial resolution of wavefront sampling can also be flexibly controlled.

Another feature for use during ophthalmic surgery is a light source for generating the wavefront that varies in output between at least two states with the wavefront returning from the eye of a patient detected in each of the "bright" state and "dark" state, to enable the rejection of signals from light other than the measurement light.

Another feature is detecting, in parallel, portions of the wavefront using a number of high-speed PSDs that can all be operated in lock-in detection mode in synchronization with the light source at a frequency above the 1/f noise range so that DC and low frequency background noises can be effectively filtered out.

Another feature is performing active parallel wavefront sampling. The active, parallel wavefront sampling elements can be controlled in terms of their position, sub-wavefront sampling aperture size, focusing power, and on/off state.

Still another feature enhances the diopter coverage range by having the sub-wavefront sampling elements spaced apart wide enough so that there is no cross talk between the wavefront sampling elements over a large refractive error measurement diopter range. In another example, only a certain number of sub-wavefronts well separated from each other are sampled by activating a subset of the sub-wavefront sampling elements and also by enabling only a corresponding number of position sensing devices/detectors (PSDs) to avoid cross talk. In still another example, the PSDs and the sub-wavefront sampling elements can be activated to respectively change their longitudinal position and/or their focusing power in response to the patient's refractive state such that the sub-wavefront tilt sensitivity for each PSD can be dynamically adjusted. In addition, the transverse position of the PSDs can also be adjusted in response to the patient's refractive state such that each PSD is positioned at the best transverse position to provide an optimized centroid position response.

Still another feature is utilizing sequentially scanning or shifting the whole wavefront so that while the parallel sub-wavefront sampling elements and the position sensing devices/detectors (PSDs) are fixed in space, any portion of the incident wavefront can be sampled. In another aspect, the scanner/deflector tracks the eye and shifts the wavefront returned from the patient's eye with automatic adjustment of the shift so that depending on the pupil size, position, and the diopter value of the wavefront from the eye, only certain desired portions of the wavefront within the patient's pupil, such as the central 3~4 mm diameter area, are sampled.

Still another feature is utilizing timely reporting of the measured eye refraction in the sense that there is low latency between any change in the refractive state and its report by the instrument. This is achieved by averaging the detected wavefront aberration data over a desired period and updating the qualitative and/or quantitative measurement result overlaying a live eye image with a desired update rate.

Still another feature provides accurate measurements over a large diopter range of refractive errors that occur during ophthalmic surgery, for example those errors that occur when the natural lens of the eye has been removed but before replacement with an artificial lens. These accurate measurements can be achieved in a number of ways. One example is to design the optics to dynamically adjust the sensitivity or the slope of the sub-wavefront tilt response curve by actively changing the distance between the sub-wavefront sampling elements and the position sensing devices/detectors, or by actively changing the focal length of the sub-wavefront focusing lenses. Another example is to dynamically offset the spherical refractive diopter value of the wavefront at an intermediate conjugate wavefront image plane using a spherical diopter value offsetting element such as a focal length variable lens.

These and other features and advantages of the example embodiments will become more readily apparent to those skilled in the art upon review of the following detailed description of the preferred embodiments taken in conjunction with the accompanying drawings. Each of these features can be used singly or in combination and with any of the embodiments described herein.

BRIEF DESCRIPTION OF THE DRAWING

FIG. 5 shows one example of sequential transverse wavefront shifting or scanning as applied to the optical configuration of FIG. 3a.

DETAILED DESCRIPTION

Figure 1:
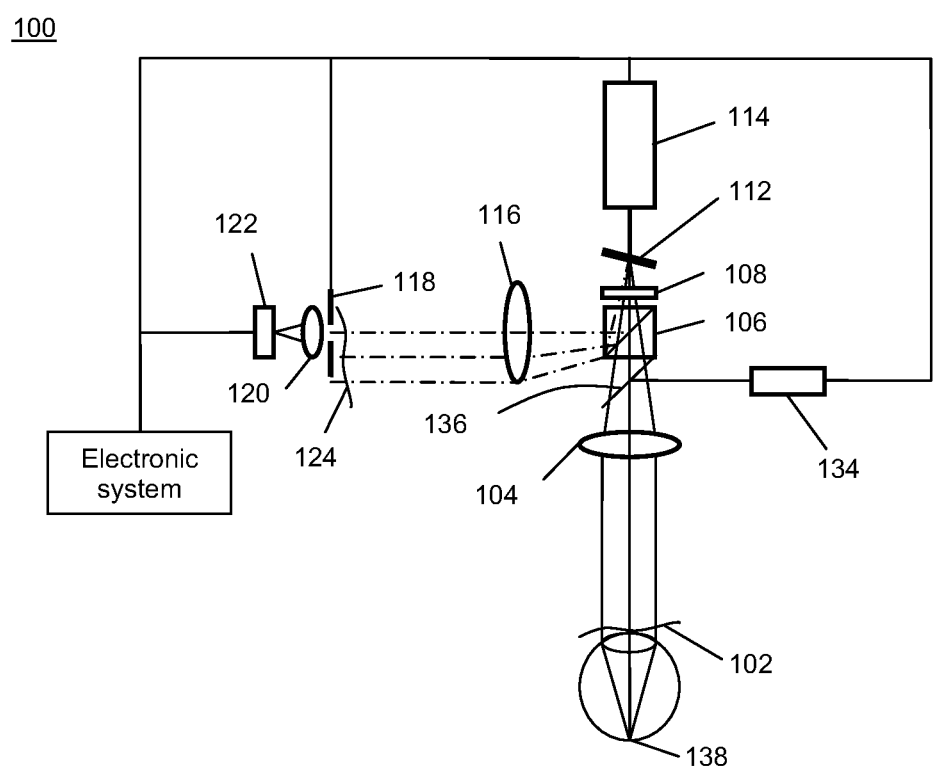
FIG. 1 shows a schematic diagram of the sequential wavefront sensor disclosed in co-assigned U.S. Pat. No. 7,445,335.

Reference will now be made in detail to various example embodiments illustrated in the accompanying drawings. While the invention will be described in conjunction with these embodiments, it will be understood that it is not intended to limit the invention to any embodiment. On the contrary, it is intended to cover alternatives, modifications, and equivalents as may be included within the spirit and scope of the invention as defined by the appended claims. In the following description, numerous specific details are set forth in order to provide a thorough understanding of the various embodiments. However, the present invention may be practiced without some or all of these specific details. In other instances, well known process operations have not been described in detail in order not to unnecessarily obscure the present invention. Further, each appearance of the phrase an "example embodiment" at various places in the specification does not necessarily refer to the same example embodiment.

Most prior art ophthalmic wavefront sensors for human eye wavefront measurements use a two dimensional CCD or CMOS image sensor for wavefront information collection. For examples, a typical Hartmann-Shack wavefront sensor (see for example, U.S. Pat. Nos. 5,777,719, 6,199,986 and 6,530,917) uses a two dimensional lenslet array and a two dimensional CCD or CMOS image sensor. A Tscherning wavefront sensor (see for example, Mrochen et al., "Principles of Tscherning Aberrometry," J of Refractive Surgery, Vol. 16, September/October 2000) projects a two dimensional dot array pattern onto the retina and uses a two dimensional CCD or CMOS image sensor to obtain the image of the two dimensional dot pattern returned from the eye to extract the wavefront information. A Talbot wavefront sensor uses a cross grating and a CCD or CMOS image sensor placed at the self-imaging plane of the cross grating (see for example U.S. Pat. No. 6,781,681) to extract the wavefront information. A Talbot Moiré wavefront sensor (see for example, U.S. Pat. No. 6,736,510) uses a pair of cross gratings with mutual rotational angle offset and a CCD or CMOS image sensor to obtain an image of the Moiré pattern to extract the wavefront information. A phase diversity wavefront sensor (see for example U.S. Pat. No. 7,554,672 and US20090185132) uses a diffraction lens element and a two dimensional CCD or CMOS image sensor to obtain images associated with different diffraction orders to extract the wavefront information.

Due to the large amount of data that needs to be collected by the two dimensional image sensor and to the limit in the frame rate resulting from the clock rate and/or the data transfer rate over an electronic data transfer line such as a USB cable, the image sensors used in all these prior art wavefront sensor devices can only operate with a relatively low frame rate (typically at 25 to 30 frames per second) and hence are sensitive to DC or low frequency background noise. As a result, these prior art wavefront sensors generally can only function in a relatively dark environment in order to reduce noise from DC or low frequency background/ambient light.

In addition, the diopter measurement range of these ophthalmic wavefront sensors are generally limited to within ±20D due in large part to a compromise in the spacing or pitch of the fixed grid wavefront sampling elements, which determines the wavefront tilt sensitivity, the wavefront diopter measurement range, and the wavefront measurement spatial resolution.

Another wavefront sensor technology based on laser beam ray tracing (see for example U.S. Pat. No. 6,409,345 and U.S. Pat. No. 6,932,475) does not absolutely require the use of a two dimensional CCD or CMOS image sensor for wavefront information extraction. However, a commercial product (iTrace from Tracey Technologies) has a limited measurement range of only ±15D, and still requires a dark environment for wavefront measurement.

Co-assigned U.S. Pat. No. 7,445,335 discloses a sequential wavefront sensor that sequentially shifts the entire wavefront to allow only a desired portion of the wavefront to pass through a wavefront sampling aperture. This wavefront sensor employs lock-in detection to reject DC or low frequency optical or electronic noise such as from background light or electronic interferences by pulsing the light source used for generating the wavefront from the eye and synchronizing it with a high frequency response position sensing device/detector (such as a quadrant detector). Therefore, this wavefront sensor does not require a dark environment for wavefront measurement, and is extremely suitable for continuous real time intra-operative refractive surgeries with the illumination light of a surgical microscope remaining always in the "on" state. Sequentially sampling a wavefront completely removes any potential cross talk issue, which therefore provides the possibility of a large wavefront measurement dynamic range. However, the optical configuration of U.S. Pat. No. 7,445,335 is not ideal for covering a large diopter range as it needs a beam scanner with a relatively large beam interception area. Another co-assigned U.S. patent application (US20120026466) discloses improved optical configurations over U.S. Pat. No. 7,445,335. These improved configurations can allow the use of a relatively small and commercially available light beam scanner (such as a MEMS scanner) to scan the whole object beam from an eye over a large diopter range (up to ±30D), and consequently, refraction of the eye in even the aphakic state can be adequately covered. By flexibly shifting the wavefront, any portion of the wavefront can be sampled and thus high spatial resolution can also be achieved.

However, due to eye safety requirement, there is a limit to the optical energy that can be delivered within a given time to a patient eye. Therefore, even with the pulsing of the light source and the lock-in detection approach to boost up signal to noise ratio, if one wants to sample a large number of spatial portions of a wavefront returned from an eye, the wavefront measurement update rate can be limited. On the other hand, if one wants to have high wavefront measurement update rate, the maximum number of spatial sampling points can be limited. There is thus a need to further improve the performance of such a wavefront sensor operating in lock-in detection mode.

In accordance with one or more embodiments of the present invention, a number of parallel wavefront sampling elements are combined with a corresponding number of image or light spot position sensing devices/detectors (PSDs) that all operate in lock-in detection mode in synchronization with the pulsing of the light source at a frequency above the 1/f noise frequency range. Each PSD has a sufficiently high frequency response so that DC or low frequency background light generated noise can be substantially filtered out and the signal to noise ratio can be boosted.

In addition to sampling the wavefront in parallel, the physical spacing of the parallel wavefront sampling elements is designed so that there is no cross talk within a desired eye refractive error diopter coverage range, Furthermore, in order to sample any portion or segment of a wavefront, the wavefront can also be sequentially shifted relative to the wavefront sampling elements using similar approaches as disclosed in co-assigned U.S. Pat. No. 7,445,335 and patent application US20120026466.

FIG. 1 shows a schematic diagram of the sequential wavefront sensor disclosed in co-assigned U.S. Pat. No. 7,445,335. A narrow beam of light from a light source 134 is directed to the retina of an eye 138 through a beam-directing element 136 such as a beam splitter. An object beam of light originating from the retina of the eye, having a wavefront 102 when leaving the eye, is focused by the first lens 104. The object wavefront beam travels through a polarization beam splitter (PBS) 106 arranged in such a manner that its pass-through polarization direction is aligned with the desired polarization direction of the object light beam. As a result, a linearly polarized object beam will pass through the PBS 106. A quarter-wave plate 108 is placed behind the PBS 106 with the fast axis oriented so that a circularly polarized light beam is emerged after the beam passes through the quarter-wave plate 108.

The object light beam that carries the wavefront information from the eye is focused on the reflective surface of a tilted scanning mirror 112, which is mounted on a motor shaft 114. The object light beam reflected by the mirror is changed to a direction that is dependent on the tilting angle of the scan mirror 112 and the rotational position of the motor 114. The reflected beam is still circularly polarized, but the circular polarization rotation direction will be changed from left hand to right hand or from right hand to left hand. Hence, upon passing through the quarter-wave plate 108 for a second time on its return path, the beam becomes linearly polarized again, but with its polarization direction rotated to an orthogonal direction with respect to that of the original incoming object beam. Therefore, at the polarization beam splitter 106, the returned object beam will be mostly reflected to the left as shown by the dashed light rays in FIG. 1.

A second lens 116 is placed on the left next to the PBS 106 to collimate the reflected object beam and to produce a replica of the original input wavefront (124) at the plane of the wavefront sampling aperture 118. Due to the tilting of the scan mirror, the replicated wavefront 124 is transversely shifted. An aperture 118 is placed in front of a sub-wavefront focusing lens 120 to select a small portion of the replicated wavefront 124. The sub-wavefront focusing lens 120 focuses the selected sub-wavefront onto a position sensing device/detector 122, which is used to determine the centroid of the focused light spot generated from the sequentially selected sub-wavefronts. By rotating the motor 114 and changing the tilting angle of the scan mirror 112, the amount of radial and azimuthal shift of the replicated wavefront can be controlled such that any portion of the replicated wavefront can be selected to pass through the aperture 118 in a sequential way. As a result, the overall wavefront of the original incoming beam can be characterized as in the case of a standard Hartmann-Shack wave-front sensor with the exception that the centroid of each sub-wavefront is now obtained in a sequential rather than a parallel manner.

As can be seen in FIG. 1, by controlling the tilt angle of the scan mirror and the rate of pulsing the light source, any portion of the wavefront can be sampled. In addition, the electronic control and detection system can synchronize the operation of the light source 134, the motor 114, the wavefront sampling aperture 118 if it is active also, and the position sensing detector 122 to enable lock-in detection. Therefore, the signal to noise ratio can be boosted up and DC or low frequency background light generated noise can be filtered out.

However, as wavefront shifting is done by a beam scanner at the optical Fourier transform plane of a 4-f optical wavefront relay system, when the refractive error diopter value of a patient eye is large, the dimension of the object beam at the Fourier transform plane will also be relatively large. This means that to cover a large diopter range, the beam scanner requires a relatively large beam interception area. In the case of cataract surgery, where the working distance between the eye and the input port is large, the required beam scanner size would not be practical in terms of cost and commercial availability.

Figure 2:
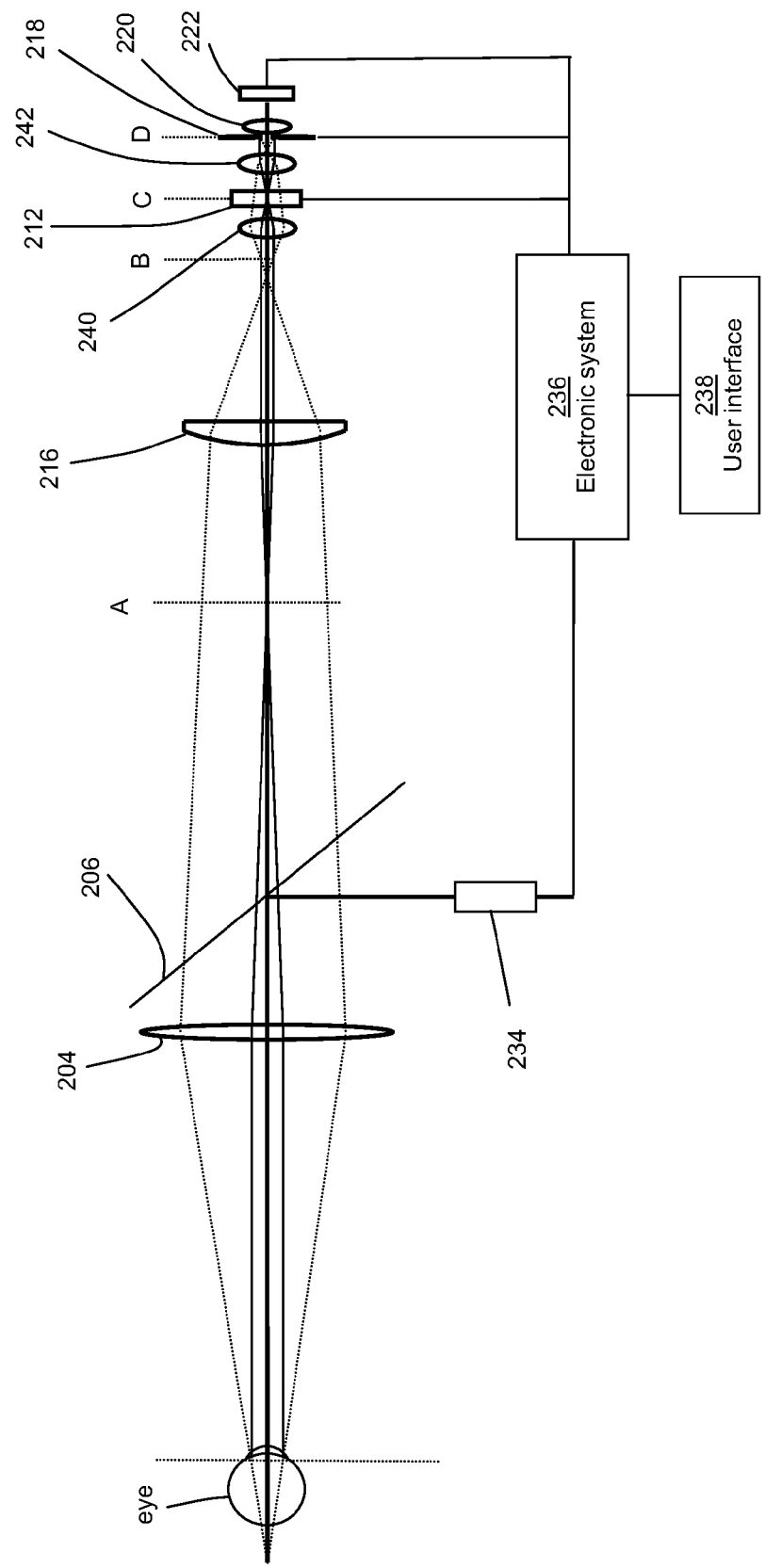
FIG. 2 shows an improved optical configuration as disclosed in co-assigned US20120026466.

FIG. 2 shows another optical configuration as disclosed in co-assigned US patent application US20120026466 that uses two cascaded 4-f relays having first and second Fourier transform planes, A and C respectively, and first and second image planes, B and D respectively. Owing to the use of two cascaded 4-f wavefront relays or an 8-f wavefront relay, sequential transverse wavefront shifting can be achieved by angularly scanning the wavefront beam at or around the second Fourier transform plane C where the wavefront beam width (over a desired large refractive error diopter measurement range) can be maintained within a certain physical dimension range so that the object beam can be completely intercepted by a relatively small beam scanner 212.

As shown in FIG. 2, after the first wavefront relay at the wavefront image plane B, the object beam width is reduced because of the difference in the focal length of the first lens 204 and the second lens 216, although the beam divergence or convergence is increased. The second 4-f wavefront relay comprises a third lens 240 and a fourth lens 242, each having a relatively large focusing power or short focal length and a relatively large numerical aperture (NA) or beam acceptance cone angle. The beam width at the second Fourier transform plane C is now relatively small. By angularly scanning the beam at the second Fourier transform plane C, the wavefront image at the second wavefront image plane D can be transversely shifted. The transversely shifted wavefront can be sampled at the second wavefront image plane D by a wavefront sampling aperture 218 and focused by a sub-wavefront focusing lens 220 onto a position sensing device/detector (PSD) 222.

Similarly to the embodiment depicted in FIG. 1, by controlling the beam scanner 212 at the second Fourier transform plane C and timing the pulsing of the light source, any portion of the wavefront can be sampled. Again, the electronic control and detection system can synchronize the operation of the light source 234, the scanner 212, the aperture 218 (if it is a variable aperture) and the PSD 222 to enable lock-in detection to boost up the signal to noise ratio and to filter out the noise generated by DC or low frequency background light.

An electronic control system 236 having a user control interface 238 is coupled to beam scanner 212 and variable aperture to allow control of these elements to vary the scanning pattern or aperture size. In other embodiments the electronic control system 236 may be coupled to other controllable elements as will be described more fully below. The user interface 238 may be in the form of buttons on the instrument, a graphical user interface (GUI) on the instrument or on a computer coupled to the electronic control system 236.

Note that in FIGS. 1 and 2, there is only one wavefront sampling element and only one position sensing device, and wavefront sampling is conducted in a pure sequential manner. In this case only one portion of the entire wavefront is sampled and therefore optical energy returned from the eye is not efficiently used.

Figure 3A:
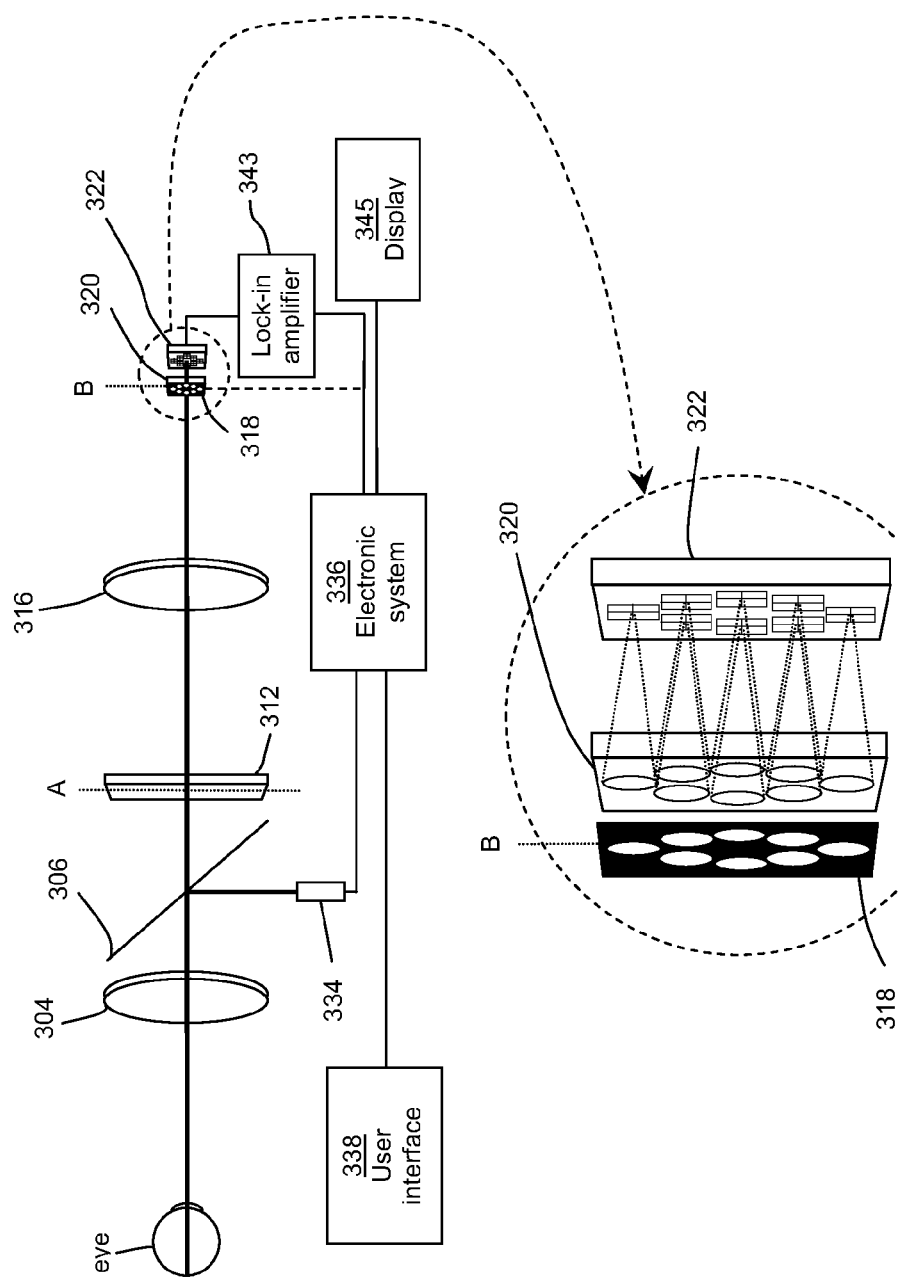
FIG. 3a shows one embodiment of an example wavefront sensor, in which a pulsed light source is synchronized with an array of position sensing devices/detectors to enable the sensor to work in both parallel sampling and also lock-in detection mode.

FIG. 3a shows an example where a beam of light from a light source 334 (such as a SuperLuminescent Diode or SLD) operating in pulse and/or burst mode is launched via a beam directing element 306 (such as a Polarization Beam Splitter (PBS)) into a patient eye to form a relatively small image spot on the retina for the generation of a wavefront that returns from the eye. The beam directing element 306 should have a large enough light beam interception size to ensure that the object beam carrying the wavefront information from the eye over a desired eye diopter measurement range is fully intercepted without being disturbed by the edge of the beam directing element.

Using a PBS can help the suppression of interference from light reflected or scattered from other undesired optical interfaces of the eye such as the cornea and the eye lens. This is because the relatively narrow input SLD light beam is linearly polarized in a first polarization direction and light reflected or scattered from the cornea and the eye lens is also mostly linearly polarized in the first polarization direction whereas the retina scattered light has a large component that is polarized orthogonal to the first polarization direction. So the PBS, as the beam directing element 306, serves as both a polarizer for the SLD beam propagating towards the eye and also as an analyzer to pass only the object beam returned from the retina in a second orthogonal polarization direction.

In addition to the need to filter out a certain polarization component, the wavefront leaving the eye also needs to be relayed to a wavefront sampling image plane. In FIG. 3a, this is achieved with a 4-f wavefront relay optical configuration comprising a first lens 304 and a second lens 316. At the wavefront image plane B, an array of sub-wavefront sampling elements comprising, for example an annular array of sub-wavefront sampling apertures 318 and a corresponding annular array of sub-wavefront focusing lenses 320, sample and focus in parallel a number of portions of the relayed wavefront at wavefront image plane B. A corresponding array of position sensing devices/detectors (PSDs) 322 (such as an annular array of lateral effect position sensing detectors or quadrant detectors) are arranged behind the array of sub-wavefront sampling elements for detecting the image spot centroid position of each sampled sub-wavefront.

In order to show the details of the sub-wavefront sampling elements and the position sensing devices/detectors (PSDs), we have included in FIG. 3a, a zoomed-in inset of the wavefront sampling and centroid detection stage optical elements, with the annular array of sub-wavefront sampling apertures 318 deliberately separated from the annular array of sub-wavefront focusing lenses 320 although in practice, they are more likely to be in contact or close proximity from each other. In the zoomed-in drawing, the annular array of PSDs 322 are arranged around the back focal plane of the sub-wavefront focusing lenses 320 to result in a relatively sharp focused image spot on the PSDs when the wavefront is planer, however, this does not have to be the case as the annular array of PSDs 322 can be arranged before or after the focal plane of the sub-wavefront focusing lenses 320. In the example embodiment, by sampling around an annular ring of the wavefront from an eye, the sphere and cylinder refractive error of the eye and the axis of the cylinder can be determined. However, the pattern of the parallel sub-wavefront sampling elements can be in other forms such as a spoke pattern or a two-dimensional linear array form.

FIG. 3a depicts a lock-in amplifier 343, coupled to receive the output signals from the array of PSDs 322, for noise suppression. A display 345 may be coupled to the electronics system 336 that receives the output of the lock-in amplifier 343. The operation of the lock-in amplifier 343 is described below with reference to FIG. 4. The electronics system 336 has processing capabilities to process the output of the lock-in amplifier 343 including applying algorithms to determine refraction, aberrations and other diagnostic or clinical factors. The display 345 could be implemented as a heads-up display in association with a surgical microscope or a large screen display or a back projection display or as part of a personal computer or workstation.

Note that as compared to prior art wavefront sensor systems, the presently described example embodiment has a number of features that when combined in one way or another make it advantageous for eye refractive surgery. Firstly, the sub-wavefront sampling elements are physically separated so that the density is generally less than the density of a standard lenslet array used in a typical Shack-Hartmann wavefront sensor. This is achieved by making the lenslet-to-lenslet distance or lenslet pitch larger or by making the diameter of each lenslet larger than that of a lenslet used in a typical Shack-Hartmann wavefront sensor. Alternatively, the focal length of the lenslets of the lenslet array can be made shorter than the focal lengths of lenslets used in a typical Shack-Hartmann wavefront sensor. As a result, a sufficiently large diopter measurement range can be covered without cross talk, i.e. the landing of a sampled sub-wavefront image spot onto a non-corresponding PSD.

Figure 3B:
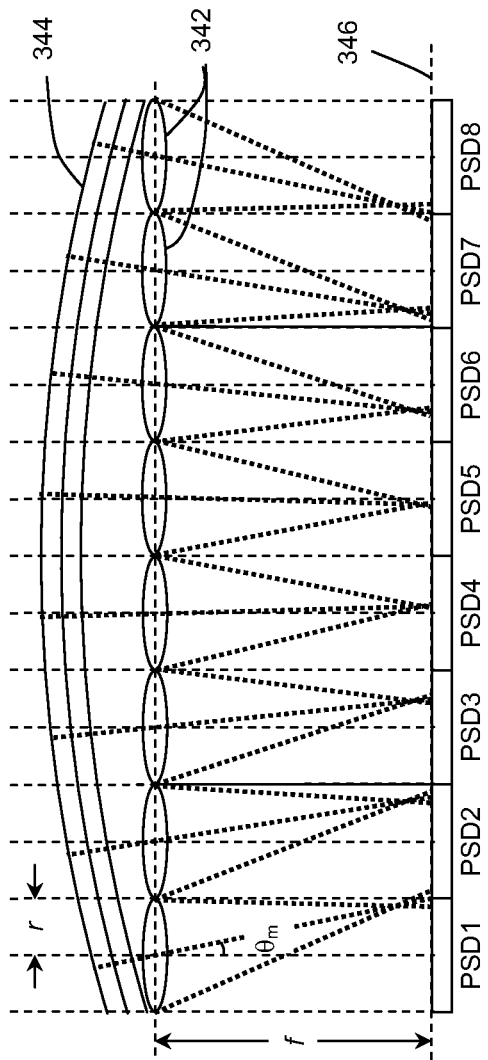
FIG. 3b shows a lenslet array of a typical Shack-Hartmann wavefront sensor with a corresponding array of position sensing devices/detectors and the maximum diopter measurement range that can be achieved without cross talk.

In order to illustrate the point, FIG. 3b shows a lenslet array of a typical Shack-Hartmann wavefront sensor with a corresponding array of position sensing devices/detectors and what happens to the maximum diopter measurement range without cross talk. In the present description, the term "cross talk" refers to a condition where a portion of or an entire light beam intended to be focused by a lenslet on a corresponding detector is focused on a neighboring detector.

The lenslet array 342 of a typical Shack-Hartmann wavefront sensor is densely packed with the lenslets arranged next to each other without any gap. In this case, there are a large number of lenslets per unit area and the sampling density for measuring a wavefront is high. Assuming that the wavefront to be measured is a spherical convergent wavefront 344 as shown, then the maximum average sub-wavefront tilt, $\theta_m$, that can be measured without cross talk will be limited by the radius r and the focal length f of each lenslet where $\theta_m = \tan^{-1}[r/f]$. FIG. 2 illustrates that the curvature of the wavefront increases for large positive or negative diopter values. Therefore $\theta_m$ indicates the maximum diopter measurement range value.

In FIG. 3b, there is an angular spread of the sub-wavefront tilt angle and the sub-wavefront sampled by the far left lenslet will be focused by this far left lenslet to form a light spot that lands at the right border of PSD1 between PSD1 and PSD2.

As can be seen, any further increase in the convergence or the absolute diopter value of the convergent spherical wavefront will cause the tilt angle to exceed $\theta_m$ and cause the light spot sampled by the far left lenslet to land beyond the border between PSD1 and PSD2 into PSD2, thereby causing cross talk. In fact, since the sampled sub-wavefront is convergent, the focused spot is actually in front of the focal plane 346, and accordingly the corresponding image spot on the focal plane 346 will be wider rather than that in sharp focus, so the sub-wavefront tilt measurement range is slightly less than $\theta_m$. A similar situation exists for the far right lenslet and the two position sensing devices/detectors PSD8 and PSD7.

On the other hand, if the wavefront is a spherical divergent wavefront, the sharply focused image spots will, in general, actually be behind the focal plane 346, so the light spot on the focal plane 346 will also be wider rather than that in sharp focus, and accordingly the sub-wavefront tilt measurement range will again be slightly less than $\theta_m$. If the wavefront is not spherical but has prismatic tilt and/or astigmatism and/or even other high order aberrations, a local sub-wavefront tilt sampled by any of the lenslets can exceed the tilt angle measurement range limit $\theta_m$.

However, if the parallel sub-wavefront sampling elements are not closely packed but are intelligently distributed with the center-to-center distance between two elements properly controlled, then it is possible to deliberately avoid cross talk and also achieve a certain desired large enough diopter measurement range.

Figure 3C:
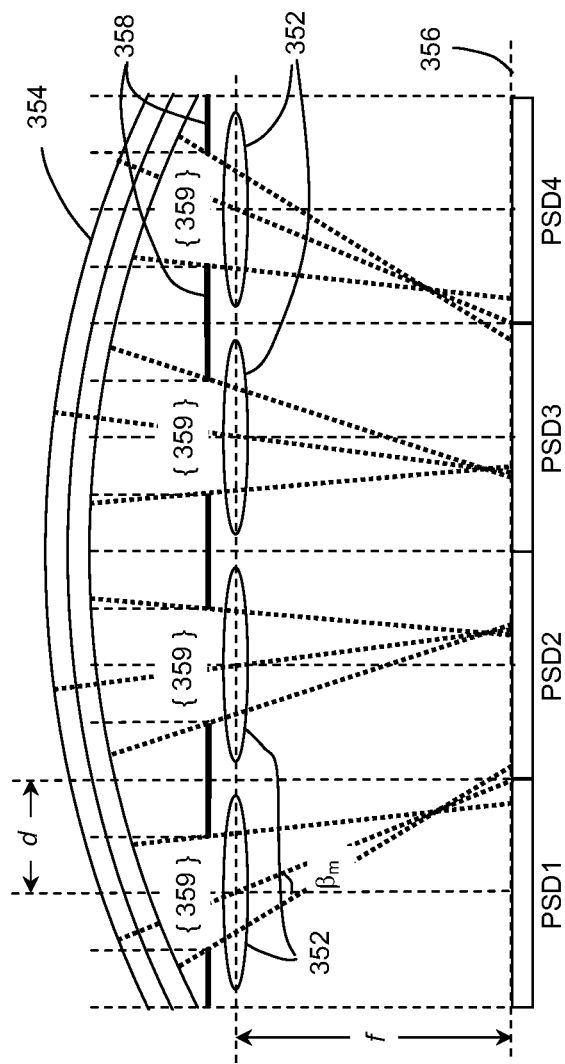
FIG. 3c shows an example arrangement of the sub-wavefront sampling elements with a corresponding array of position sensing devices/detectors and the maximum diopter measurement range that can be achieved without cross talks.

FIG. 3c shows an example embodiment of an arrangement of the sub-wavefront sampling elements with a corresponding array of position sensing devices/detectors and illustrates that the maximum diopter measurement range without cross talk can be increased. In the illustrated example, each sub-wavefront sampling element comprises a lenslet 352 and an aperture 359 in front of the corresponding lenslet. In other words, a patterned aperture array mask 358 is combined with a corresponding lenslet array 352 to act as an array of parallel sub-wavefront sampling elements. Assuming that the focal length of each lenslet is the same as that shown in FIG. 3b and is represented by the same f, whereas now the distance from the center of one lenslet to the border or mid-point between two sub-wavefront sampling elements is d as shown, then the maximum average sub-wavefront tilt that can be measured without cross talk will now be $\beta_m = \tan^{-1}[d/f]$. Since d is greater than r, the local sub-wavefront tilt measurement range is thus increased. In fact, FIG. 3c shows a more convergent spherical wavefront 354 that is being sampled than the wavefront depicted in FIG. 3b with the limitation imposed by $\beta_m = \tan^{-1}[d/f]$. Clearly, the absolute diopter value of the convergent spherical wavefront 354 in FIG. 3c that can be sampled without cross talk is higher than that of the wavefront 344 of FIG. 3b.

In FIG. 3c the widths of the PSDs are increased as compared to the width of the PSDs in FIG. 3b, i.e., d is greater than r. The use of wider PSDs instead of narrow PSDs with spaces between them larger is to ensure that with an increase in the sub-wavefront tilt the light spot landing on a corresponding PSD can be captured by the corresponding PSD. Otherwise, if the PSD has the same smaller size as that shown in FIG. 3b but were spaced apart, then an increase in the sub-wavefront tilt could cause the sub-wavefront light spot land in the space between the photo-sensitive area of the PSDs. In other words, the light spot would not be captured by the PSD to produce an electrical signal.

Also in FIG. 3c the lenslets have larger diameter compared to the diameter of the lenslets in FIG. 3b but have the same focal length. Designing a larger lenslet with the same focal length has the advantage that when such a lenslet is combined with a variable aperture, varying the size of the aperture can provide flexibility in controlling the size of the sub-wavefront to be sampled over a larger sampling size range. For example, for refractive error measurement which only involves the determination of the sphere and cylinder diopter values and the cylinder axis, a larger sub-wavefront sampling size can provide the benefit of averaging as well as reducing the burden of data processing. In other words, the high spatial wavefront sampling density as would normally be provided by a standard Shack-Hartmann wavefront sensor can be an overkill for that type of refractive measurement and can substantially increase the data capturing, transferring and processing time, thus slowing down the operation of the wavefront sensor and making it too slow for real time refractive surgical procedure applications.

On the other hand, if only a small area of a cornea needs to be operated on using for example, a LASIK system, the laser ablation spot size on the cornea is generally much smaller than the size of a typical lenslet of a Shack-Hartmann wavefront sensor. In such a case, the aperture depicted in FIG. 3c can be made correspondingly small enough and wavefront scanning as will be discussed below can be employed to allow non-averaged wavefront sensing over a small cornea area so that very high measurement precision can be achieved in terms of high order wavefront aberration measurement. In fact, in some example embodiments the aperture array is made active in the sense that the aperture size can be actively controlled. It should be noted that the patterned aperture array can also be arranged after the patterned lenslet array and may not be absolutely required as their function can be served by the diameter of the lenslet.

Further, in view of the formula for calculating $\theta_m$ it is seen that the sub-wavefront tilt measurement range without cross talk, $\theta_m$, can also be increased by choosing a smaller focal length value f. In such a case, the size of each PSD can be smaller to still provide the sub-wavefront tilt measurement range. However, the tilt measurement sensitivity will also suffer because for the same amount of change in the sub-wavefront tilt there will be a smaller displacement of the light spot on the PSD as is well known to those skilled in the art.

In order to provide even more flexibility, some example embodiments use a lenslet array having variable focal length or a lenslet array with certain sub-groups of the lenslet array having different focal lengths. The longer focal length sub-group of lenslets can provide better sensitivity while the shorter focal length sub-group of lenslets can provide larger sub-wavefront tilt measurement dynamic range. There can be two or three or more sub-groups of lenslets and accordingly two or three or more sets of position sensing detectors arranged at different distances from the lenslets.

A significant problem with existing wavefront sensors used in vision correction procedures is detecting the wavefront returned from the eye in the presence of background optical or electronic noise. Examples of problematic background noise components are ambient light incident on the detector and 1/f noise generated by the detector itself, and other radiated or conducted electronic noises. Both of these background noise components have significant amplitudes at the frame rate of standard two dimensional CCD/CMOS image sensors.

In some of the example embodiments the light source used for creating the object wavefront from the eye is operated in pulse and/or burst mode. The pulse repetition rate or frequency is higher than the typical frame rate of a standard two dimensional CCD/CMOS image sensor. For example, the pulse rate of the light source in this example embodiment can be in or above the kHz range. For a CCD/CMOS image sensor the frame rate is typically about 25 to 30 frames per second. The PSDs of the present disclosure are two-dimensional position sensing devices/detectors (PSDs), all with sufficiently high temporal frequency response so that they can be operated in lock-in detection mode in synchronization with the pulsed light source at a frequency above the 1/f noise frequency range. The electronic control and detection system is coupled to at least the light source and the array of PSDs and is configured to phase lock the operation of the light source and the parallel PSDs. The electronic control and detection system can also be coupled to an array of variable sub-wavefront sampling apertures to further control the sampling aperture size if the sampling apertures are active.

Figure 4:
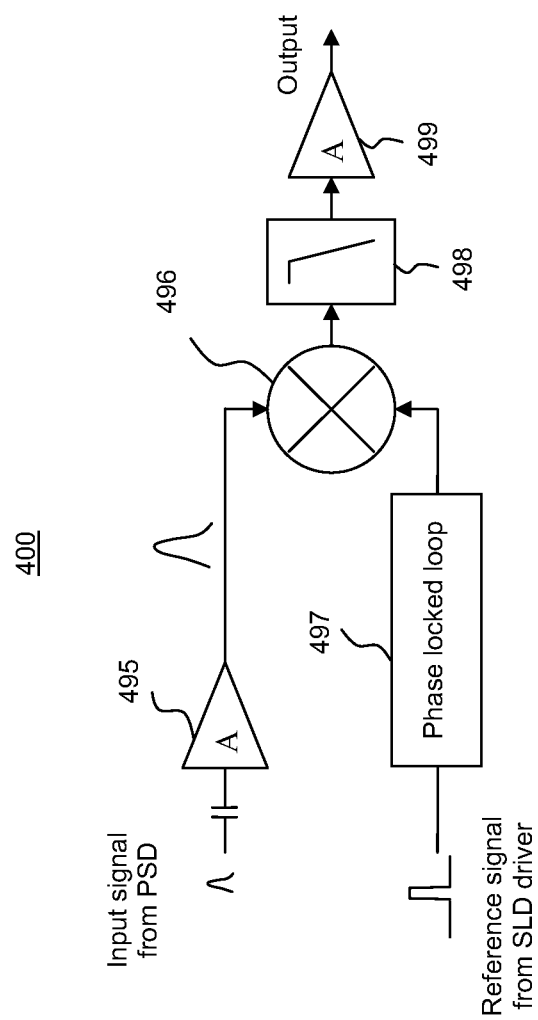
FIG. 4 is a block diagram showing one example embodiment of a lock-in detection amplifier.

FIG. 4 is a block diagram showing one example embodiment of a lock-in detection amplifier 400. Note that phase sensitive lock-in detection is a powerful synchronous detection technique well known to those skilled in the art for the recovery of small signals which can be obscured by noise much larger than the signal of interest. A mixer 496 has a first input coupled to the output of a preamplifier 495 having a signal from the PSD A.C.-coupled to its input. The mixer 496 has a second input coupled to the output of a phase-locked loop 497 which is locked to the reference signal that drives and pulses the SLD. The input signals are mixed (multiplied) by the mixer 496 to form a mixer output signal. The output of the mixer 496 is passed through a low-pass filter 498 and amplified by an output amplifier 499 to form the output of the lock-in detection amplifier 400.

The operation of the lock-in detection amplifier will now be described. The input signal from the PSD to the preamplifier 495 includes a component at the reference frequency which indicates the deflection of the sub-wavefront measured by the position-sensor detector. The amplitude of this component is the desired output of the lock-in detection amplifier. The input signal from the PSD also includes noise signals at low frequency such as the frequency of the ambient light and 1/f noise from the detector.

The input to the phase-locked loop (PLL) is a signal having substantial amplitude only at the reference frequency.

The amplitudes of input signals to the mixer are multiplied. Each frequency component of the amplified PSD signal is converted into a first mixer output component at a frequency equal to the sum of the frequency of a PSD frequency component and the reference frequency and a second mixer output component at a frequency equal to the difference of the frequency of the PSD frequency component and the reference frequency.

The low-pass filter 498 passes signals having a frequency near zero (a D.C. signal) and blocks signals having frequencies greater than those near zero (A.C. signals). All noise components at frequencies other than the reference frequency are blocked because both the sum and the difference of the noise frequency and the reference signal are not equal to zero so both mixer output components are A.C. signals and are blocked by the low-pass filter.

The frequency of the first mixer output signal for the frequency component of the PSD signal at the reference frequency is equal to the sum of the reference frequency with itself which is twice the reference frequency and thus is an A.C. signal that is blocked by the low-pass filter. However, the frequency of the second mixer output signal for the frequency component of the PSD at the reference frequency is equal to the difference of the reference frequency and itself which is zero. This is a D.C. signal that is passed by the low-pass filter.

Accordingly, the output of the lock-in amplifier is a measure of only the frequency component of the PSD signal at the reference frequency. All noise signals at different frequencies are blocked by the low pass-filter. The low-pass filtered signal can be further amplified by another amplifier 499 for analog to digital (A/D) conversion further down the signal path.

It should be noted that each PSD can have more than one photosensitive area (for example 4 as in the case of a quadrant detector) corresponding to more than one photodiodes or photo-detectors. When implementing parallel lock-in detection the number of channels needed is the number of parallel PSDs times the number of photo-detection signal lines of each PSD. With parallel sampling, we can simultaneously collect a number of sub-wavefront samples across the wavefront.

Not shown in FIG. 4 is the A/D converter and the rest of the electronic detection and control module. Activating the A/D converter at the same frequency as the signal pulsing the SLD can also allow the collection of both dark and light samples before and during the SLD pulse to further remove the effects of electromagnetic interference as well as ambient light from the room or the microscope on which the device may be mounted.

Note that prior art wavefront sensors generally do not operate the light source in pulse and/or burst mode (at least at a frequency range above the 1/f noise region, i.e. around and beyond the kHz range) because either the light source for wavefront sensors used in astronomy, such as a distant star in space, is beyond control (see for example, U.S. Pat. No. 6,784,408) or there is no advantage of operating the light source in pulse or burst mode because a typical CCD/CMOS image sensor does not have a high enough frame rate to be operated in the above 1/f noise frequency range.

A Hartmann-Shack wavefront sensor can be operated by selectively blocking some of the lenslets of the Hartmann-Shack lenslet array (see for example, U.S. Pat. No. 7,414,712) to cover a large diopter measurement range. However, this approach is expensive and still suffers from the same limitation that the image sensor used is scanned at a low frame rate.

In the present described example embodiments, the sub-wavefront sampling elements are preferably physically separated from each other at the wavefront image plane B as shown by the zoomed-in inset in FIG. 3a. Note that in the example embodiment of FIG. 3a, each sub-wavefront sampling element comprises an aperture and a focusing lenslet. However, the focusing lenslet can either be directly used to function as an aperture or can even be removed. In the latter case, the sampled sub-wavefront beam will not be focused but will still land as a light spot on a corresponding PSD with a different centroid position for a different sub-wavefront tilt although the aperture size needs to be generally smaller than the PSD size in order to avoid cross talk.

Also in order to separately show the array of sub-wavefront sampling apertures and the array of sub-wavefront focusing lenses, the inset drawing of FIG. 3a has deliberately separated the two from each other. In practice, it is more likely that they will be arranged in close proximity. The large diopter measurement range is ensured by physically designing the spacing of the sub-wavefront sampling elements such that within the designed large diopter coverage range the tilt of any sampled sub-wavefront will not be focused to land on its neighboring PSD.

In example embodiments, higher energy efficiency can be achieved while, at the same time, the 1/f noise can be substantially reduced thereby allowing DC or low frequency background noise such as noise generated by the illumination light of a surgical microscope to be effectively filtered out.

These features make the presently described example wavefront sensor, when integrated with or attached to an ophthalmic surgical microscope, extremely suitable for a vision correction surgical procedure such as cataract surgery. A cataract surgeon can perform the surgery without stopping half way to turn off the illumination light of the surgical microscope and waiting for the capture of multi-frames of data and for the processing of the data in order to obtain a refraction measurement.

With the present example embodiments, the diopter measurement dynamic range can be made large enough (for example, up to ±30D) for the refractive state of even an aphakic eye to be fully covered. Furthermore, by sampling just a properly selected number of sub-wavefronts around an annular ring of the wavefront from a patient eye, one can obtain the sphere and cylinder diopter values as well as the cylinder axis as needed for the selection of an intra-ocular lens (IOL) and for the confirmation of, for example, emmetropia or an intended sphero diopter value of a pseudo-phakic eye. By properly selecting the wavefront sampling number around each annular array, the required data transfer rate and data processing resources can be substantially reduced.

Example embodiments will now be described that provide more spatial sampling points and/or higher spatial resolution as can normally be provided by prior art ophthalmic wavefront sensors, although this may not be absolutely needed for a cataract surgery. These embodiments can also measure higher order aberrations as well as to possibly provide a two dimensional wavefront map. These example embodiments include an angular light beam scanner 312 (such as a transmissive electro-optic or magneto-optic beam deflector) that can be arranged at the Fourier transform plane A of the 4-f relay as shown in FIG. 3a to transversely shift or scan the wavefront at the wavefront image plane B relative to the array of sub-wavefront sampling elements. In doing so, one can achieve sub-aperture spatial resolution as has been disclosed in U.S. Pat. No. 6,376,819 and also sample those portions of the relayed wavefront between the sampling apertures if the relayed wavefront is otherwise static.

Figure 5:
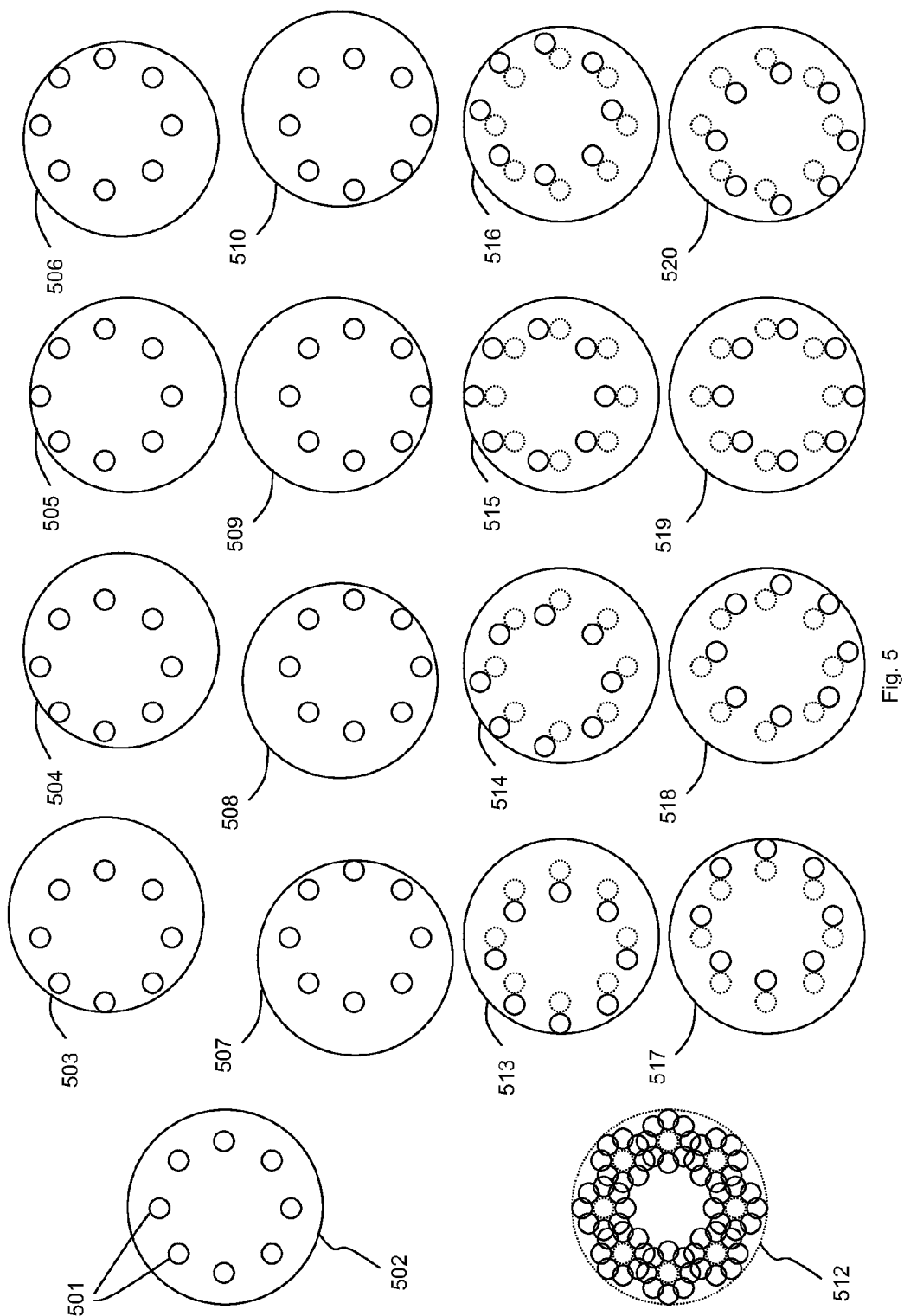

FIG. 5 shows one example of sequential transverse wavefront shifting or scanning as applied to the optical configuration of FIG. 3a. In this example, 8 sub-wavefront sampling lenslets 501 are arranged in the form of an annular array at the wavefront image plane B with sufficient spacing between any two neighboring lenslets such that there is no cross talk over the intended refractive diopter measurement range. The relayed wavefront is shown as a circular disk 502 with the 8 lenslets 501 sampling 8 portions of the relayed wavefront. Without any wavefront shifting or scanning, the 8 sampled sub-wavefronts are rotationally symmetric with respect to the wavefront image 502.

The circles 502-520 represent a first portion of a relayed wavefront that is incident on the array of lenslets. The location of the circle, i.e., the first portion of the wavefront, is scanned to different positions as shown in the various drawings that allow sub-portions of the first portion to be sampled.

Of the 4 rows shown on the right part of FIG. 5, the top two rows (503 to 510) show one example of the effect of sequentially transversely shifting the relayed wavefront relative to the 8 lenslets. From 503 to 510, the relayed wavefront is shown to have been sequentially shifted by the same distance respectively to the right, the right-bottom, the bottom, the bottom-left, the left, the left-top, the top, and the top-right directions.

The bottom two rows (513 to 520) show the equivalent result of moving the lenslet array relative to the wavefront instead of moving the wavefront relative to the lenslet array. The 8 dotted line circles in each case from 513 to 520 show the original sampling position of the 8 lenslets with respect to the non-shifted first portion of the relayed wavefront.

From 513 to 520, the 8 solid line circles show the equivalent relative movement of the 8 lenslets with respect to the original lenslet positions if the first portion of the relayed wavefront is treated as stationary. The total sampling pattern 512 resulting from the shifting depicted in the top two rows shows the cumulative sampling effect.

From the total sampling pattern 512, it can be seen that without wavefront shifting only the original 8 annular array sub-portions of wavefront will be sampled and that with wavefront shifting other sub-portions of the wavefront can be sampled.

In the illustrated example, sampling overlaps are shown as can be seen in the total sampling pattern 512. This indicates that spatial sampling resolution smaller than the sampling aperture size (which in this illustrated example is the lenslet diameter) can be achieved. In fact, one can control the scanning angle of the scanner 312 to achieve any desired spatial sampling resolution as long as the beam scanner can be controlled to whatever desired practically achievable angular precision. In addition, the total sampling pattern 512 also shows that as a result of transversely shifting the relayed wavefront, not only can portions of the non-shifted wavefront between any two neighboring lenslets be sampled, but also that portions of the wavefront towards the center and away from the center of the non-shifted wavefront can also be sampled. In the total sampling pattern 512 it can already be seen that, if needed, three annular rings can be sampled. Any portion of the wavefront can be sampled by controlling the beam shifter 312.

It should be noted that the array of the sub-wavefront sampling elements do not need to be in the form of an annular array as illustrated in FIG. 3a. For example, they can be in the form of a rectangular array as long as they are physically well separated from each other to ensure that a large enough refractive error diopter measurement dynamic range can be covered without cross talk. Alternatively, they can be more closely spaced as long as the focal length of the lenslet behind each sub-wavefront sampling aperture is correspondingly shorter and the distance between the lenslets and the PSDs is correspondingly reduced. It should also be noted that the number of lenslets does not need to be restricted to 8 and can be any number arranged in any form.

Figure 6:
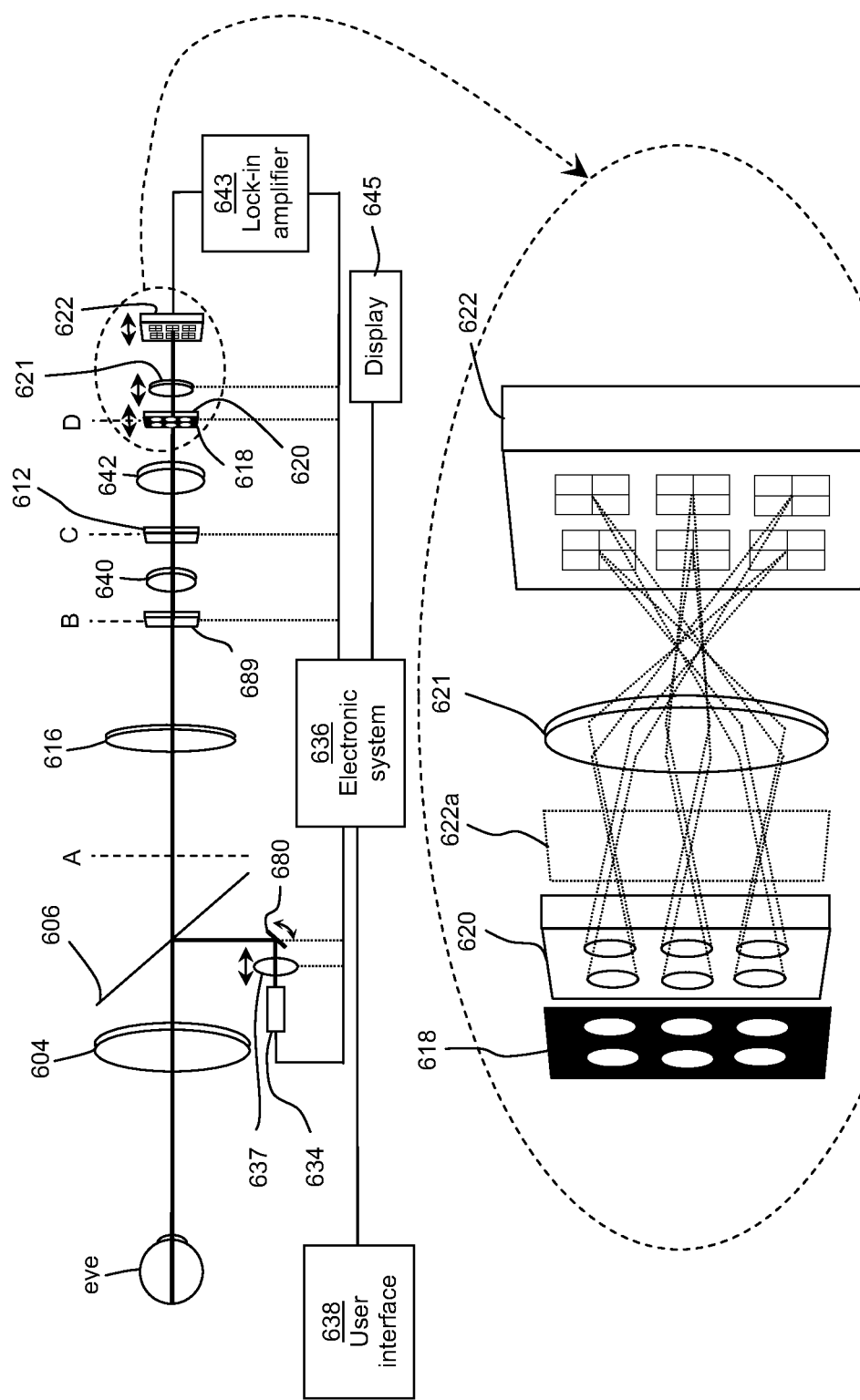
FIG. 6 shows another embodiment of the wavefront sensor of FIG. 3a, in which an 8-f wavefront relay configuration is combined with a small beam scanner to enable practical sequential wavefront scanning in addition to parallel wavefront sampling and lock-in detection.

As discussed before in comparing the configuration of FIG. 1 to that of FIG. 2, if scanning is to be implemented with a 4-f relay then the beam scanner 312 will need to have a large beam interception window size. To overcome this limitation and also provide other various improvements, FIG. 6 shows another example embodiment. As can be seen from FIG. 6, the optical configuration is, in some aspects, similar to that shown in FIG. 2. However, there are a number of new features that can be implemented either individually or in combination with others.

In the example embodiment of FIG. 6 a relatively narrow beam of light from a light source 634 (such as a superluminescent diode (SLD)) operating in pulse and/or burst mode is launched through a focus adjustable lens 637 and directed by a beam directing element 606 (such as a polarization beam splitter or PBS) to a patient's eye for generating a wavefront returned from the eye. The focusing change from the lens 637 can be utilized to ensure that the spot size of the light beam when landing on the retina is relatively small for various refractive states of the eye. In addition, a scan mirror 680 for scanning the SLD beam can be arranged at a back focal length distance of the first lens 604 so that the SLD beam scanner position is conjugate to the retina of an emmetropic eye. In this way, an angular scan of the SLD beam scanner 680 will cause a transverse scan of the SLD beam with respect to the cornea plane but still allow the SLD beam to land on the same retina location if the eye is emmetropic. This scanner can be used to scan the SLD beam to follow any eye movement so that SLD beam can always enter the eye from the same cornea location.

Instead of using a 4-f wavefront relay as shown in FIG. 3a, an 8-f wavefront relay system comprising a first lens 604, a second lens 616, a third lens 640 and a forth lens 642 is used to relay the wavefront from the pupil or cornea plane through an intermediate wavefront image plane B to a final wavefront image sampling plane D. Such an 8-f wavefront relay can be considered as comprising two cascaded 4-f relays. The first relay includes the first and second lenses that guide the wavefront relay beam through a Fourier transform plane A to the intermediate wavefront image plane B. The second relay includes the third and fourth lenses that further relay the wavefront from the intermediate wavefront image plane B through a Fourier transform plane C to the final wavefront image plane D. The benefit of such an 8-f wavefront relay optical configuration has been discussed with reference to FIG. 2 and more details can be found from co-assigned patent application US20120026466.

Instead of using only one sub-wavefront sampling element and one PSD as shown in FIG. 2, an array of sub-wavefront sampling elements comprising, for example, a rectangular array of apertures 618 and a corresponding rectangular array of sub-wavefront focusing lenslets 620, can be disposed substantially at the final wavefront image plane D to sample and focus a desired array of sub-wavefronts. Again, the sub-wavefront sampling elements can be physically separated from each other and/or the focal length of the lenslet array can be properly selected in such a way that a large refractive error diopter measurement range can be covered without cross talk.

These elements can be combined with a corresponding array of parallel PSDs to detect the image spot centroid positions of the sampled array of sub-wavefronts, and to achieve parallel wavefront sampling with lock-in detection by synchronizing the detectors with the pulsed light source.

As an alternative to directly arranging the PSDs substantially at the back focal plane of the lenslets behind the sub-wavefront sampling elements, a lens 621 can be used to relay and also preferably optically magnify the virtual image spots formed at a virtual image spot plane 622a, as shown in the inset of FIG. 6, to a new plane of real PSDs 622 as is well known to those skilled in the art (see for example U.S. Pat. No. 6,595,642).

This lens 621 is especially useful if a relatively high density lenslet array with a shorter focal length is used to cover a desired large diopter range. Typically, such a lenslet array has a relatively small pitch, i.e., the spacing between the centers of the lenslets in that array, of, for example 0.5 mm to 1.0 mm, whereas each PSD can be relatively large (for example, in the case of a quadrant detector, about 5 mm in diameter). Therefore, to achieve a one-to-one correspondence, the image spots formed by the lenslet array can be optically magnified and relayed by the lens 621 to a larger pitch array to increase the distance between two neighboring PSDs so that the PSDs can be arranged to physically fit on a substrate.

As in the case of FIG. 2, a small size beam scanner or deflector 612 can be arranged at the second Fourier transform plane C to fully intercept and angularly scan the whole object beam that carries the eye wavefront information over a desired large refractive error diopter range. However, compared to FIG. 2, the needed beam angular scan or deflection range can now be substantially lessened. This is because with the use of an array of sub-wavefront sampling elements, one only needs to scan the object beam within an angle range such that the transverse wavefront shift at the final wavefront image plane D equals the pitch, i.e., distance between the centers of adjacent PSDs in the sub-wavefront sampling element array in both the x and y directions. In this way, all the wavefront portions incident between any two sub-wavefront sampling elements can be sampled if the relayed wavefront is otherwise not scanned. This will allow different types of beam scanners to be used in addition to a reflective MEMS scanner, such as, for example, a transmissive electro-optic or electro-magnetic scanner that generally can only cover a relatively small angular scanning range.

Similar to the case of FIG. 3a, a lock-in amplifier 643 can be coupled to receive the output signals from the array of PSDs 622 for noise suppression. A display 645 may be coupled to the electronics system 636 that receives the output of the lock-in amplifier 643. The electronics system 636 has processing capabilities to process the output of the lock-in amplifier 643 including applying algorithms to determine refraction, aberrations and other diagnostic or clinical factors. The display 645 could be implemented as a heads-up display in association with a surgical microscope or a large screen display or a back-projection display or as part of a personal computer or workstation.

Figure 7:
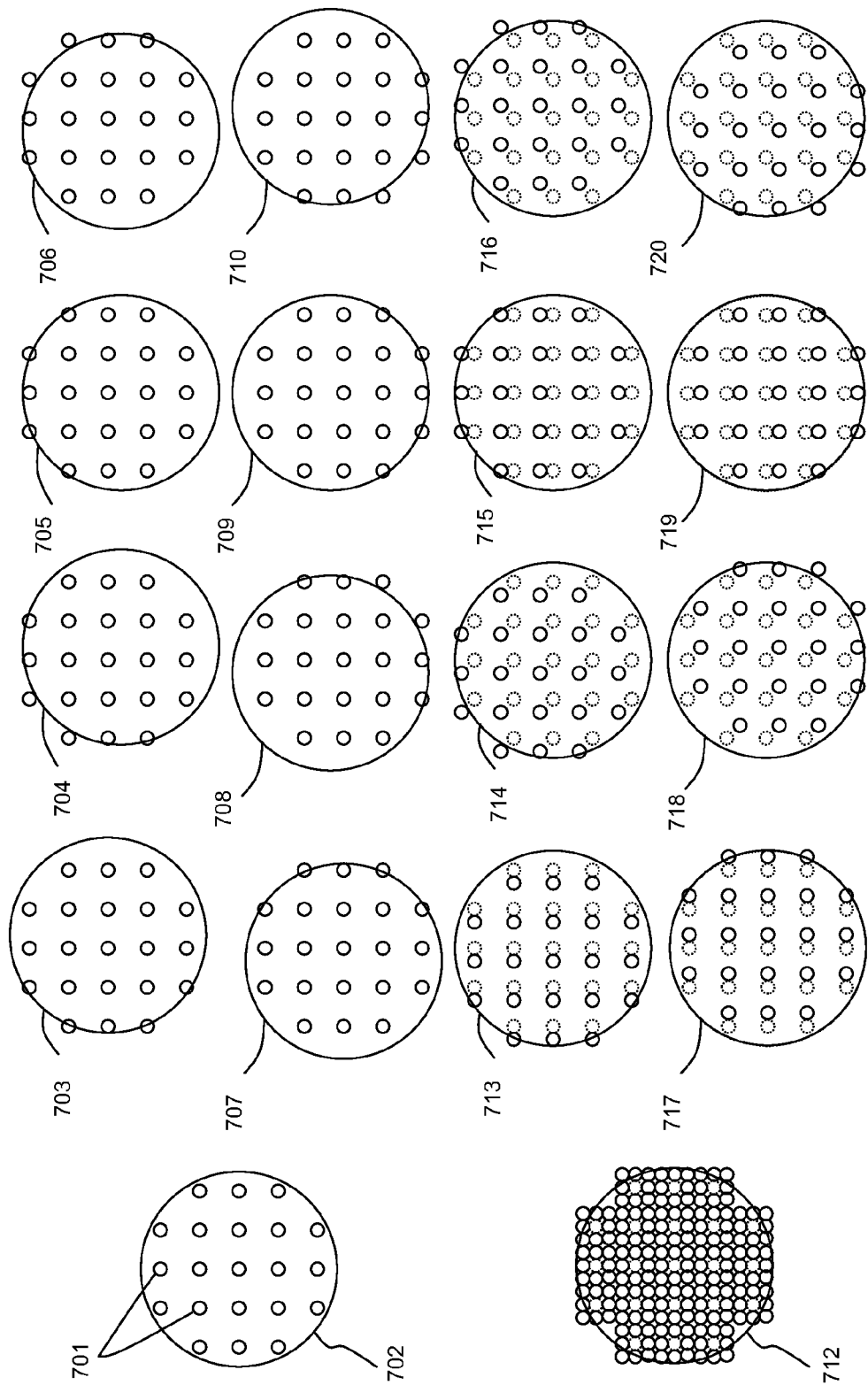
FIG. 7 shows one example of sequential transverse wavefront shifting or scanning as applied to the optical configuration of FIG. 6.

FIG. 7 shows one example of sequential transverse wavefront shifting or scanning as applied to the optical configuration of FIG. 6. In this example, 21 sub-wavefront sampling lenslets 701 are arranged in the format of a two dimensional linear array at the wavefront image plane D with sufficient spacing between any two neighboring lenslets such that there is no cross talk over the intended refractive error diopter measurement range. As in FIG. 5, the first portion of the relayed wavefront is shown as a circular disk 702 incident on the lenslet array with the 21 lenslets 701 sampling 21 sub-portions of the first portion relayed wavefront. Without any wavefront shifting or scanning, the 21 sampled sub-portions of the first portion of the relayed wavefronts are regularly distributed in a two dimensional array format with respect to the relayed wavefront 702.

Of the 4 rows shown in FIG. 7, the top two rows (703 to 710) show one example of what happens when the relayed wavefront is sequentially transversely shifted relative to the 21 lenslets. From 703 to 710, the first portion of the relayed wavefront is shown to have been sequentially shifted by the same distance in either the horizontal and/or the vertical direction, respectively to the right, the right-bottom, the bottom, the bottom-left, the left, the left-top, the top, and the top-right directions.

The bottom two rows (713 to 720) show the equivalent result of moving the lenslet array relative to the wavefront instead of moving the wavefront relative to the lenslet array. The 21 dotted line circles arranged in a two dimensional linear array format in each case from 713 to 720 show the original sampling position of the 21 lenslets with respect to the non-shifted first portion of the relayed wavefront. From 713 to 720, the 21 solid line circles show the equivalent relative movement of the 21 lenslets with respect to the original lenslet positions when the first portion of the relayed wavefront is treated as stationary. The total sampling pattern 712 shows the cumulative sampling effect. From the total sampling pattern 712, it can be seen that without wavefront shifting the original 21 lenslet portions of the relayed wavefront will be sampled and with wavefront shifting, regions around the original 21 lenslets can be sampled.

In fact, the illustrated example shows a transverse shift in either the horizontal and/or the vertical direction by a distance equal to the diameter of each lenslet and the original pitch or spacing between two horizontal or vertical lenslets is made equal to three times the diameter of each lenslet. In other words, the gap distance is equal to twice the diameter of each lenslet. As a result, the illustrated scanning enables one to achieve sampling of the relayed wavefront as if the wavefront has been sampled by a closely packed two dimensional linear lenslet array as in the case of a typical Hartmann-Shack wavefront sensor.

It should be noted that one can control the scanning angle of the beam scanner 612 and the pulsing of the SLD to realize sampling at smaller transverse wavefront shift distances and hence to achieve any desired spatial sampling resolution. In addition, the illustrated example also shows that with the use of a two dimensional linear array of sub-wavefront sampling elements the beam scanner 612 needs only to scan a small angle range in the horizontal and vertical directions in order to allow all portions of the relayed wavefront to be sampled.

Note that the array of wavefront sampling apertures and/or PSDs can also be made active. The aperture size for sampling the sub-wavefronts can be dynamically adjusted utilizing, for example variable diaphragm arrays or a liquid crystal based aperture size variable array. The apertures can also be active in the sense that different portions of the relayed wavefront image can be directed to different PSDs using a MEMS mirror array as disclosed in U.S. Pat. No. 6,880,933. The focal length of the sub-wavefront focusing lens can also be varied using, for example, include liquid crystal microlens arrays and flexible membrane based liquid lens arrays. In addition, the position of the PSDs or the position of the sub-wavefront focusing lenslet array can also be longitudinally moved.

In the example embodiments of both FIG. 3a and FIG. 6, there is an electronic system that is coupled to at least the light source and the PSDs to phase-lock the operation of the light source and the PSDs at a frequency above the 1/f noise frequency range so that DC or low frequency background noises can be substantially filtered out. In addition, the electronic system can also be coupled to the focus variable lens 637 for controlling the focus of the SLD beam, to the SLD beam scanner 680, to the wavefront object beam scanner/deflector 612, to the aperture array 618, to the lenslet array 620, and to the lens 621. These electronic couplings are meant to control the operation of the coupled elements or devices.

Further, although in FIGS. 3a and 6 the SLD beam is launched from behind the first lens, the SLD beam can be launched from anywhere between the eye and the final wavefront image plane D (such as in front of the first lens or even behind the second lens) and its beam divergence or convergence can also be adjusted by other means in addition to the focus variable lens 637 (such as using an axially movable lens) to ensure that a desired light spot is formed on the retina of various eyes.

The pulsing of the light source is to be interpreted as encompassing all kinds of temporal modulation of the light source. For example, the SLD can be modulated between on/off or dark/bright states; it can also be modulated between a first light level state and a second light level state; the SLD can also be modulated in a sinusoidal manner. Another example is to have the light source operated in a burst mode to create a stream of light pulses, in which each pulse is also modulated by a carrier or modulation frequency. Accordingly, lock-in detection or synchronized detection should be interpreted as any phase locking or coherent detection means. The lock-in detection can be at both the high carrier frequency and/or at the pulse repetition rate/frequency.

The optical path for launching the SLD beam and also for guiding the returned object beam can be folded in various ways to save space and make the wavefront sensor module compact. This means that there can be mirrors or other optical beam folding elements used to fold the various optical paths. The beam scanner can be either transmissive or reflective. In addition to a 1:1 ratio wavefront relay, there can be optical magnification or demagnification of the wavefront from the eye to the intermediate wavefront image plane and to the final wavefront sampling image plane. This means that the focal length of all the lenses being used for relaying the wavefront can be of different values. In addition to two cascaded 4-f wavefront relays, there can be more cascaded 4-f or other wavefront relays.

Due to the fact that the intermediate wavefront image plane B of FIG. 6 is conjugate to the object wavefront plane and the final wavefront image plane D, a wavefront compensator or defocus offsetting element 689 can be located at plane B and controlled by the electronics system. In doing so, the wavefront sensor system can be converted into an adaptive optics system for various other applications. In addition to simply fully compensating the overall wavefront aberration as is normally done for an adaptive optics system, one can also either partially or full compensate only one or some of the wavefront aberrations to allow the remaining uncorrected wavefront aberrations to exhibit themselves more pronouncedly and hence to be more precisely measured. For example, the degree of sphere defocus can be fed back to the compensator or offsetting element 689 that affects the divergence or convergence of the detected wavefront. This feedback can change the measured defocus so it forms a closed-loop system and closed-loop control techniques may be used to bring the divergence or convergence of the measured wavefront to any desired value, most likely to bring the value near zero so that the wavefront is substantially planar. In addition, the information about the sign and degree of defocus can be used to adjust the variable focus lens 637 that affects only the divergence or convergence of the SLD beam to form an open-loop control system.

The spatial arrangement of the sub-wavefront sampling elements and the associated PSDs do not need to be arranged with a regular constant pitch or in an annular array or a rectangular array format but can be in any format. For example, there can be two or more annular ring arrays with the outer annular array sub-wavefront sampling elements spaced farther apart than those of the inner annular array(s).

Moreover, the transverse position of the PSDs can also be actively changed in response to the refractive state of a patient eye. For example, when the eye is aphakic, the wavefront from the eye at the corneal plane is generally relatively highly divergent and this wavefront, when relayed to the final wavefront image plane, will also be highly divergent. In this case, if an annular ring array of sub-wavefront sampling elements are used to sample the relayed wavefront, the corresponding annular array of PSDs can be moved radially outward with respect to the annular ring array of sub-wavefront sampling elements so that, if the relayed wavefront is a perfect spherically divergent wavefront, the image or light spot centroid of each sampled sub-wavefront is at or near the center of each corresponding PSD. In this way, any additional wavefront tilt deviation from the imagined perfect spherically divergent wavefront can be detected with high precision as only the central portion of each PSD is used for centroid detection. In addition, it should be noted that the lenslet array 320 or 620 (FIGS. 3a and 6) may not be absolutely needed as in the case of a Hartmann Shack wavefront sensor versus Hartmann wavefront sensor, because a Hartmann array of holes will also work.

Still further, a spatial light modulator (SLM) can also be combined with a high density lenslet array and the SLM can be operated in synchronization with the light source and also the PDS array so that only a selected number of apertures are opened over a selected number of lenslets during a light source on period. For example, one or more annular array(s) of lenslets can be opened and the decision on which annular array is opened can be made depending on the sphere or defocus diopter value of the object wavefront. Accordingly, a desired annular array of wavefront sample data will be collected. Sampling around only one annular array will give only refractive errors but not high order aberrations, which will be sufficient for cataract surgery applications. With sequential scanning or the opening of different lenslets, high order aberrations can be measured.

In addition to lateral-effect position sensing detectors and quadrant detectors/sensors, other types of PSDs can be used that operate at sufficiently high frequency and determine the centroid position of a sampled sub-wavefront image spot. For example, each PSD can be a cluster of 3 or more photodiodes. Each PDS of the PSD array can also be some clustered pixels of a high speed two dimensional image sensor that has a high frame rate, although such an image sensor will likely be expensive. Each PSD of the PSD array can also be a CMOS image sensor programmed to only output data from a certain number of pixels of a programmed region of interest (ROI) with global shutter exposure operation. Currently, a conventional large pixel count image sensor can generally only be programmed to output data from one ROI. But this does not mean that there is no possibility in the future to simultaneously output multiple ROIs' data at high enough frame rates with global exposure control. When this possibility becomes a reality, one can directly use a single two dimensional image sensor to allocate a corresponding array of ROIs as if they are an array of PSDs operating in lock-in detection mode with high enough temporal frequency response. The pulse turn-on time can be synchronized with the camera exposure. In other words, the light source can be turned on for a short duration within the time that the camera is collecting light. Alternatively, the SLD source can be turned on for a slightly longer time than the camera exposure time so that the effective pulse duration is determined by the camera exposure time.

In addition to standard lock-in detection, double sampling can also be employed to further reduce noise. For example, the light source can be modulated between a bright state and a dark state. The PSD array can record the signal of the image spots formed by focusing sub-wavefronts during the bright state and also record a background signal during the dark state. When the background signal is subtracted from the signal recorded during the bright state, the result is an improved estimate of the desired centroid of the image spots. In one example, a cluster or a number of clusters of pixels of a CCD/CMOS image sensor can be programmed as one or more regions of interests (ROIs) at act as an array of PSDs and each ROI can be further divided into bright state sub-rows and sub-columns and dark state sub-rows and sub-columns. Every other sub-row and sub-column can be sampled at every other bright and dark period. In this way, bright and dark sampling can be achieved by the same ROI or PSD at a higher frame rate as fewer pixels are used per frame. One half of the pixels in each ROI can be synchronized to the pulse "on" of SLD light and the other half can be synchronized to the pulse "off" of SLD light.

Alternatively, the electronic signal from the PSD array can be sampled at a frequency ten or more times higher than the light source pulsing frequency, converted to a digital signal and then digitally filtered. Once converted to a digital signal, other digital signal extraction algorithms such as Kalman filtering can also be employed.

Still further, in addition to the conventional 4-f or 8-f wavefront relay configuration shown in FIGS. 3a and 6, any optical wavefront relay configuration such as that disclosed in US20100208203 can be used.

Figure 8:
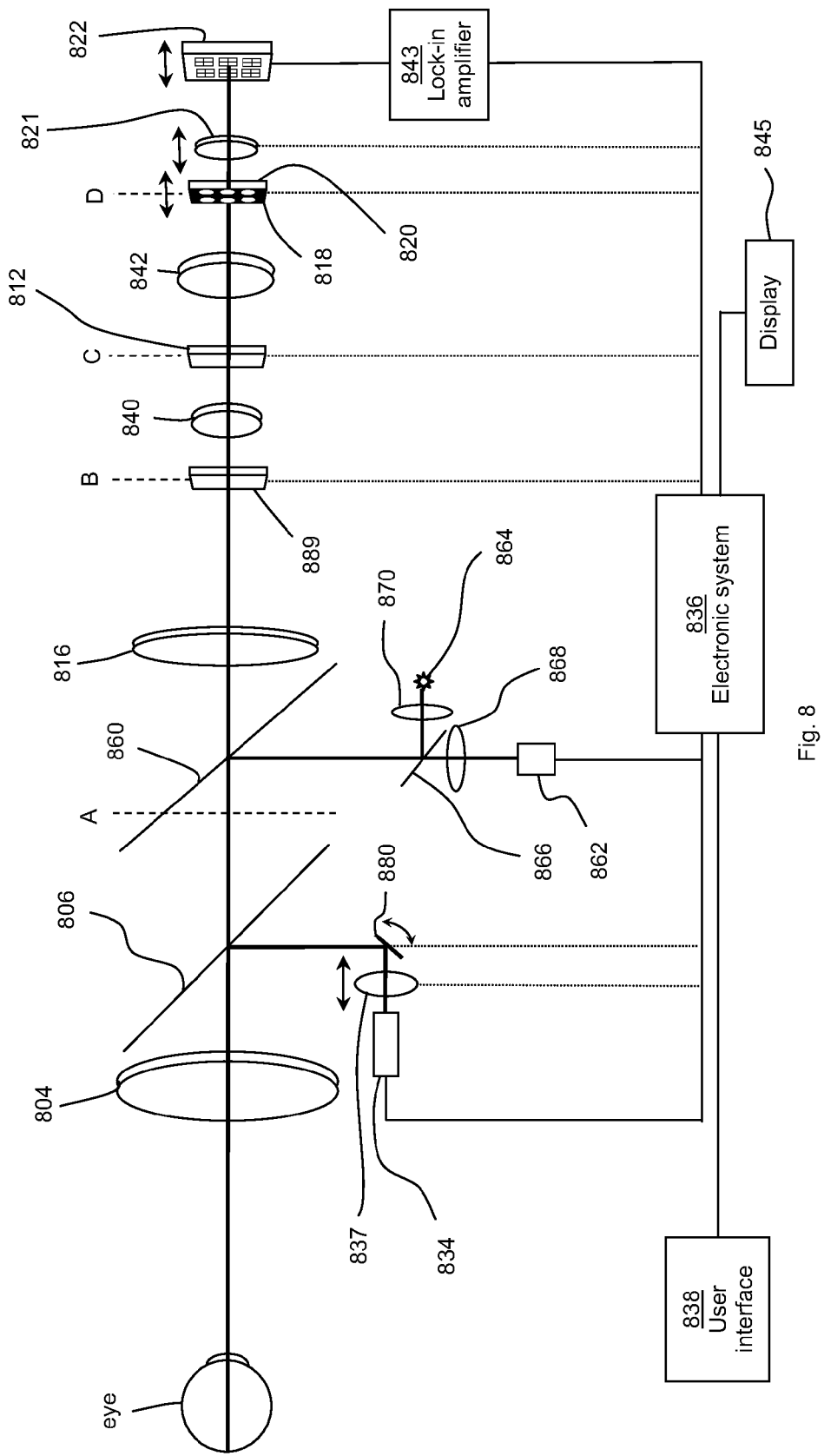
FIG. 8 shows an example of the incorporation of a fixation light source and an eye image sensor into the configuration of FIG. 6.

Other functions can also be added to the described example embodiments. FIG. 8 shows an embodiment in which a dichroic or long-wavelength-pass beam splitter 860 is employed to reflect at least a portion of light for general eye imaging and eye fixation and to substantially transmit the SLD spectral range near infrared light for wavefront sensing. The dichroic or long-wavelength-pass beam splitter 860 should have a large enough light interception window to ensure that the wavefront from the eye over a desired eye diopter measurement range is fully intercepted without being disturbed by the edge of the beam splitter window.

The reflection of the dichroic or long-wavelength-pass beam splitter can serve two functions. The first is to direct the visible or near infrared spectral portion of light returned from the eye to an image sensor 862 so that a live eye pupil image can be processed and displayed to serve various purposes such as helping a clinician in aligning the eye with respect to the wavefront sensor. The source of the light returned from the eye is an illumination light source used, for example, in a surgical microscope, ambient room light or light emitted directly from the wavefront sensor module. The second function is to direct an image of a visible fixation target 864 to the patient eye so that the eye can have a target on which to fixate if such fixation is needed.

Further down this reflected light beam path is a small beam splitter 866 that splits/combines the fixation target light beam and the image sensor light beam. This small beam splitter 866 can have various spectral properties. For example, it can be a simple 50:50 broad band beam splitter designed to operate in the visible and/or near infrared spectral range. However, if the fixation light source 864 has a relatively narrow spectral width, then, for better optical efficiency, the reflection spectrum of this small beam splitter 866 can be made to match the fixation source spectrum to allow good reflection of the fixation light and to transmit the rest of the spectrum to the image sensor 862.

The lens 868 in front of the image sensor 862 can be designed to provide the desired optical magnification for the live image of the anterior or iris or pupil of the patient's eye on a display. It can also be a dynamic lens used to adjust the focal length if needed to ensure that the image sensor plane is conjugate with the eye pupil plane so that a clear eye pupil image can be obtained. It can also be a zoom lens so that the clinician/surgeon can use it to focus on either the cornea or the retina and to change the magnification as desired. Digital zooming can also be employed here.

The lens 870 in front of the fixation target 864 can be designed to provide the patient's eye with a comfortable fixation target of a desired size and brightness. It can also be used to adjust the focal length to ensure that the fixation target is conjugate with the retina of the eye, or to fixate the eye at different distances or even to fog the eye per the need of the clinician/surgeon. The fixation light source 864 can flash or blink or change colors at a rate desired to differentiate it from, for example, the illumination light of a surgical microscope. The fixation target 864 can be an image such as a hot air balloon back illuminated by a light source or a micro-display which can display desired patterns, including arrays of dots, under control of a clinician/surgeon. In addition, the micro-display based fixation target can also be used to guide the patient to gaze in different directions so that a 2D array aberration map of the eye can be generated which can be used to assess the visual acuity of a patient's non-central or peripheral vision.

The fixation target, the eye anterior image, and/or other information could also be transmitted back to the microscope and made visible through the oculars (not shown). This information would be projected coaxially with the observer's line of sight by way of a dichroic or beam splitter through a series of lenses or physical distance that would be coplanar to the microscope or bio-microscopes working distance.

The image sensor 862 can be a black/white or color CMOS/CCD image sensor and the fixation light source can be a red or green or other color light emitting diode (LED) with its output optical power dynamically and/or manually controllable, based on different background lighting conditions. For example, when a relatively strong illumination beam from a surgical microscope is turned on the brightness of the fixation light source can be increased to enable the patient to easily find the fixation target and fixate on it.

In addition to providing a live eye pupil image, the image sensor signal can also be used for other purposes. For example, the live image can be displayed on a heads-up display or displayed on a semi-transparent micro-display incorporated in the eye piece of a surgical microscope.

The live image can be used to detect the size and transverse position of the eye pupil. When it is found that the size of the pupil is small and/or moved relative to the wavefront sensor the mechanism for selecting and/or sampling and/or shifting the wavefront can be driven using the information from the image sensor to sample only a region of the wavefront centered on the patient's pupil. In other words, the pupil size and location information can be used in a closed loop manner for the automatic and/or dynamic adjustment and/or the scaling of wavefront sampling. Thus the active wavefront sampling apertures and/or the scanner can implement eye tracking. This capability of continuously tracking the pupil using internal adjustments and without moving the wavefront sensor and/or the surgical microscope to which the wavefront sensor is attached or otherwise interfering with its use enables continuous measurement of the patient's wavefront error through the surgical procedure.

The wavefront sensor itself can also provide information for pupil tracking because the intensity of light in the sampled wavefront falls off at the edge of the patient's pupil, i.e., where the iris begins to block light returning from the retina. Thus the intensity detected by the wavefront sensor can provide a map of the patient's pupil, which can be used to center the wavefront sampling more accurately on the patient's pupil.

In addition, either the image sensor or the wavefront sensor derived eye pupil position information can be used to provide a feed back signal to drive the scan mirror 880 to enable the SLD beam to follow the eye movement so that the SLD beam always enters the cornea from the same cornea location as intended to prevent, for example, the specularly reflected SLD beam returned by the cornea from entering the wavefront sensor's PSDs. The SLD beam can also be imaged by the image sensor for centering of the eye or for intentionally offsetting the SLD beam from the center of the pupil or for providing feedback/guidance to determine the position of the eye relative to the SLD beam. The object beam scanner 812 can also be tuned with a proper offset to follow the eye pupil movement.

Furthermore, when it is found that there are obstructions in the optical path, such as when the eye is being irrigated with water, or optical bubbles are present, or the eye lid, facial skin, a surgeon's hand, or a surgical tool or instrument is in the image sensor's view field and is blocking the wavefront relay beam path, then the wavefront data can be abandoned to exclude the "dark" or "bright" data and, at the same time, the SLD 834 can be turned off.

In some example embodiments, a qualitative and/or quantitative wavefront measurement result can be overlaid onto the display of the live eye pupil image captured by the image sensor 862. Furthermore, the wavefront measurement result overlaying the live eye pupil image can be updated at a rate so that there is low latency between any change in the refractive state and the report of the changed refractive state by the wavefront sensor. This updating can be achieved by averaging the detected wavefront data over a desired period and updating the qualitative and/or quantitative measurement result overlaying the live eye image with a desired update rate that is preferred by a surgeon.

It should be noted that the image sensor can be individually incorporated into the configuration of either FIG. 3a or FIG. 6 to operate independently of the fixation target. Meanwhile, the fixation target can also be individually incorporated into the configuration of either FIG. 3a or FIG. 6 to operate independently of the image sensor.

Figure 9:
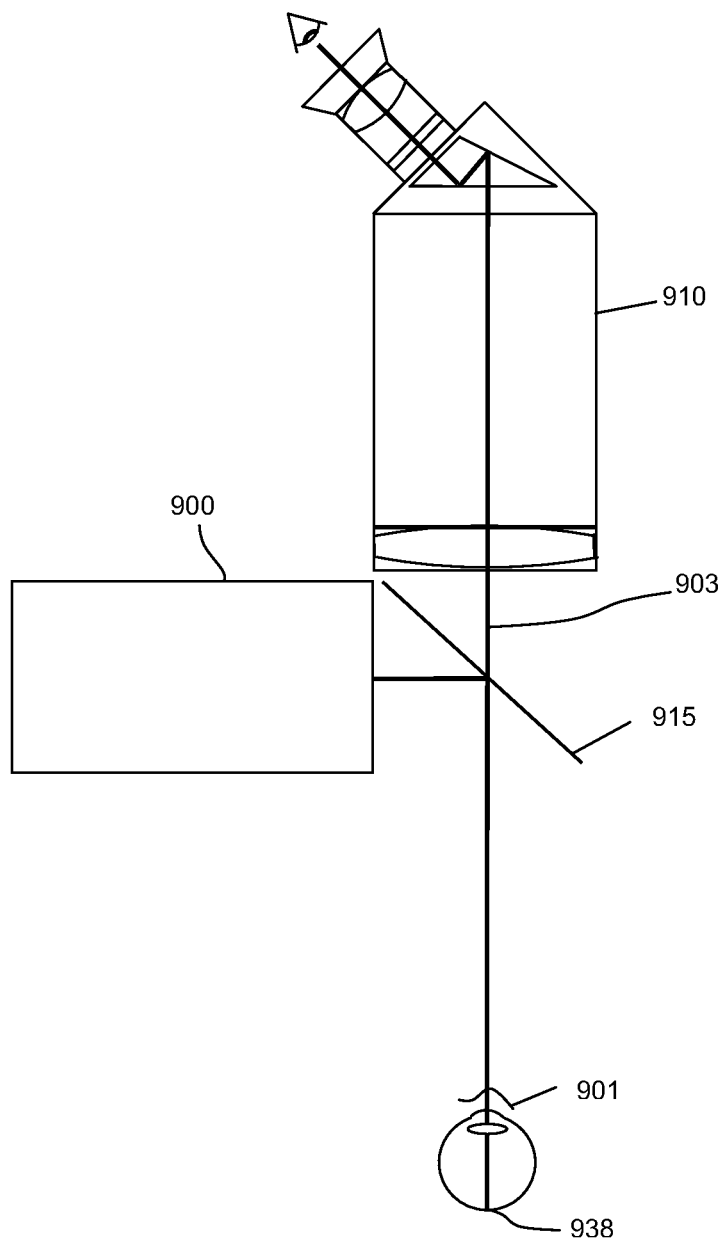
FIG. 9 shows an example of the integration of the presently disclosed wavefront sensor with a surgical microscope.

In should also be noted that the wavefront sensor of the example embodiments can be integrated with various ophthalmic instruments for eye wavefront measurements. FIG. 9 shows one example of its integration with a surgical microscope 910 which allows the viewing of a patient's eye while the eye wavefront is continuously being measured. In this integration, a beam-splitter 915 is inserted along the line of sight 903, from the eye of the microscope user to the patient's eye, to create a second optical path linking the wavefront-measurement system 900 and patient's eye 938. Preferably the beam-splitter 915 is a dichroic beam-splitter reflecting near infrared light while allowing most of the visible spectrum to pass through to the user of the microscope.

With this configuration, the wavefront measurement system 900 can emit light, preferably near infrared light, toward the retina of patient's eye 938 from which some of the scattered light will be returned from the retina to the wavefront sensor. The scattering point on the retina returns some light, with a wavefront 901, which is relayed to the wavefront sampling plane of the wavefront measurement system 900, and its deviations from a plane or from the inherently aberrated wavefront of the wavefront sensor module if there is inherence wavefront aberration reveal the aberrations or the refraction of the patient's eye.

Figure 10:
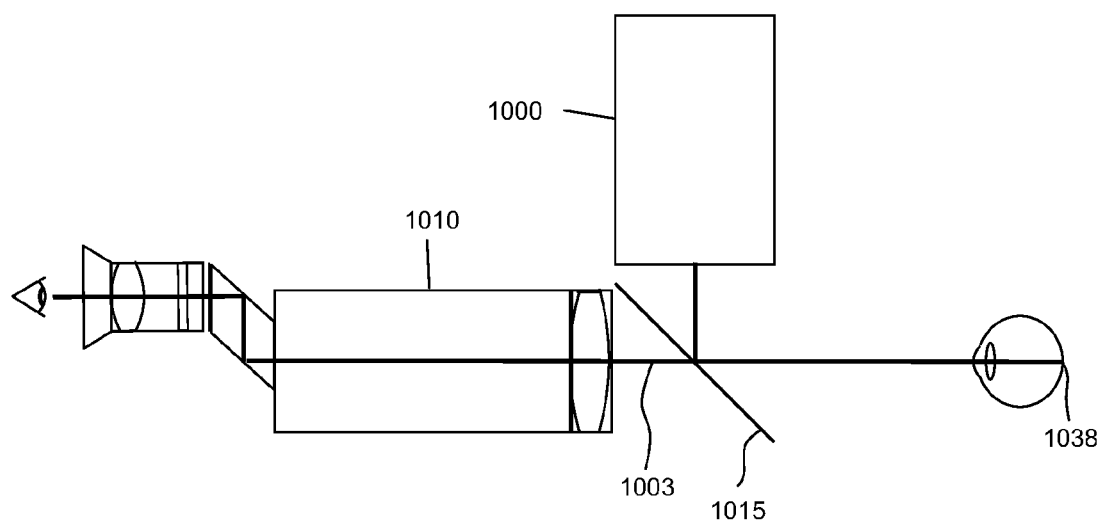
FIG. 10 shows an example of the integration of the presently disclosed wavefront sensor with a slit-lamp bio-microscope.

FIG. 10 shows the integration of the presently disclosed wavefront sensor with a slit-lamp bio-microscope. Again, a beam-splitter 1015 can be inserted along the line of sight 1003 from the eye of the slit-lamp bio-microscope user to the patient's eye, to create a second optical path linking the wavefront-measurement system 1000 and patient's eye 1038. Note that the same design of the wavefront sensor can be used in each application, although a different design with a different working distance and the associated changes is also an option depending on the requirement of a particular ophthalmic instrument.

In practice, preferably the same design of the wavefront sensor is used both with a slit-lamp bio-microscope for patient examination before and after surgery and with a surgical microscope during refractive surgery. We use the term 'ophthalmic instrument' to refer to either type of ophthalmic microscope and/or other ophthalmic instrument such as a fundus camera. Preferably, the wavefront sensor should not require special alignment or focusing of the microscope or otherwise interfere with normal use of the ophthalmic instrument.

In addition, the example embodiments of the wavefront sensor can also be integrated with a femto-second laser or an excimer laser that is used for LASIK or natural eye lens fracturing as well as cornea incision/cutting. The live eye image and the wavefront signal can be combined to indicate if optical bubble(s) or other optical non-uniformity is/are present in the eye or anterior chamber before, during and after an eye surgical operation. The wavefront information can also be used to directly guide the LASIK procedure in a closed loop manner.

These embodiments can also be deployed to measure optics, eye spectacles or glasses, IOL and/or guide the cutting/machining devices that create the optics.

These embodiments can also be adapted to microscopes for cell and/or molecular analysis or other metrology applications. The example embodiments can also be used for lens crafting, spectacle confirmation, micro-biology applications etc.

Although various example embodiments that incorporate the teachings of the present invention have been shown and described in detail herein, those skilled in the art can readily devise many other varied embodiments that still incorporate these teachings.

What is claimed is:

1. An ophthalmic wavefront sensor comprising:
   a light source configured to receive a reference signal oscillating/pulsing at a reference frequency and to generate a beam of light formed by pulses of light at the reference frequency;
   a beam directing element configured to launch the beam of light from the light source into a patient eye and where a portion of the beam of light returned from the patient eye forms an object wavefront in the form of light pulses at the reference frequency;
   an optical wavefront relay system, configured to relay an object wavefront from an object plane located at the anterior portion of a patient eye to a wavefront image plane along a beam path that can guide an incident wavefront relay beam having a large diopter range at the object plane to the wavefront image plane;
   an array of high frequency response position sensing devices with each position sensing device configured to detect the amount of deflection of an image spot centroid from a reference position and to output a measurement signal indicating the amount of deflection;
   an array of sub-wavefront sampling elements, disposed before the array of high frequency response position sensing devices and substantially at the wavefront image plane, with each sampling element in the array of sub-wavefront sampling elements configured to sample a sub-wavefront of the relayed wavefront and to focus a sampled sub-wavefront onto a corresponding high frequency response position sensing device in the array of high frequency response position sensing devices, where the sub-wavefront sampling elements are physically spaced from each other in such a way that each sampled sub-wavefront of a high diopter range object wavefront is focused only on the corresponding high frequency response position sensing device corresponding to the sub-wavefront sampling element; and
   an electronic frequency-sensitive detection system coupled to receive the reference signal and the measurement signal, with the electronic frequency-sensitive detection system configured to indicate only the magnitude of a frequency component of the measurement signal at about the reference frequency so that all noise signals, including 1/f noise, can be substantially suppressed, where f represents DC and frequencies lower than the reference frequency.

2. The ophthalmic wavefront sensor of claim 1 with the optical wavefront relay system including first and second lenses, each lens having a diameter, a focal length and an optical axis, with the optical wavefront relay system configured to relay the object wavefront from the object plane located at the anterior portion of the patient eye to a Fourier transfer plane located between the first and second lenses and to the wavefront image plane along the beam path where the focal lengths and diameters of the first and second lenses are selected to guide the incident wavefront relay beam having a large diopter range at the object plane to the wavefront image plane.

3. The wavefront sensor of claim 2 further comprising a first beam scanner disposed at the Fourier transform plane located between the first and second lenses, and configured to shift the relayed wavefront relative to the array of sub-wavefront sampling elements.

4. The wavefront sensor of claim 3 where the first beam scanner is configured to track the eye so that only desired portion(s) of the wavefront from the eye is(are) always sampled even when the eye moves.

5. The wavefront sensor of claim 3 further comprising a second beam scanner, configured to track the eye by directing the light beam for generating the object wavefront to follow the eye.

6. The wavefront sensor of claim 5 with the second beam scanner disposed at the back focal plane of the first lens of the optical wavefront relay system.

7. The wavefront sensor of claim 1 further comprising an eye image sensor configured to provide a live eye anterior image and a second directing element configured to provide an optical path for eye imaging.

8. The wavefront sensor of claim 7 further comprising a display configured to display a live eye anterior image with an overlay of a qualitative and/or quantitative result of a wavefront measurement.

9. The ophthalmic wavefront sensor of claim 1, further comprising:
   a lens disposed between the array of sub-wavefront sampling elements and the array of position sensing devices, configured to relay and optically magnify the spacing between image spots formed by the array of sub-wavefront sampling elements at an image spot plane to the plane where the array of position sensing devices are disposed.

10. An ophthalmic wavefront sensor comprising:
    a light source configured to receive a reference signal oscillating/pulsing at a reference frequency and to generate a beam of light formed by pulses of light at the reference frequency;
    a beam directing element configured to launch the beam of light from the light source into a patient eye and where a portion of the beam of light returned from the patient eye forms an object wavefront in the form of light pulses at the reference frequency;
    a first optical wavefront relay system, configured to relay an object wavefront from a first object plane located at the anterior portion of a patient eye to a first wavefront image plane along a first beam path that can guide an incident wavefront relay beam having a large diopter range at the object plane to the first wavefront image plane;
    a second optical wavefront relay system having a second object plane located substantially at the first wavefront image plane, configured to further relay the object wavefront from the second object plane to a second wavefront image plane along a second beam path that can guide the incident wavefront relay beam having a large diopter range at the first object plane to the second wavefront image plane;

an array of high frequency response position sensing devices with each position sensing device configured to detect the amount of deflection of an image spot centroid from a reference position and to output a measurement signal indicating the amount of deflection;

an array of sub-wavefront sampling elements, disposed before the array of high frequency response position sensing devices and substantially at the second wavefront image plane, with each sampling element in the array of sub-wavefront sampling elements configured to sample a sub-wavefront of the relayed wavefront and to focus a sampled sub-wavefront onto a corresponding high frequency response position sensing device in the array of high frequency response position sensing devices, where the sub-wavefront sampling elements are physically spaced from each other in such a way that each sampled sub-wavefront of a high diopter range object wavefront is focused only on the corresponding high frequency response position sensing device corresponding to the sub-wavefront sampling element; and an electronic frequency-sensitive detection system coupled to receive the reference signal and the measurement signal, with the electronic frequency-sensitive detection system configured to indicate only the magnitude of a frequency component of the measurement signal at about the reference frequency so that all noise signals, including 1/f noise, can be substantially suppressed, where f represents DC and frequencies lower than the reference frequency.

11. The ophthalmic wavefront sensor of claim 10 with the first optical wavefront relay system including first and second lenses, each lens having a diameter, a focal length and an optical axis, where the focal lengths and diameters of the first and second lenses are selected to guide the wavefront relay beam having a large diopter range at the first object plane to the first wavefront image plane; and the second optical wavefront relay system including third and fourth lenses, each lens having a diameter, a focal length and an optical axis, where the focal lengths and diameters of the third and fourth lenses are selected to further guide the incident wavefront relay beam having a large diopter range at the first object plane to the second wavefront image plane.

12. The ophthalmic wavefront sensor of claim 11 with the third lens configured to guide the object wavefront to a Fourier transfer plane located between the third and fourth lenses.

13. The wavefront sensor of claim 12 further comprising a first beam scanner, disposed at the Fourier transform plane between the third lens and the fourth lens, configured to shift the relayed wavefront relative to the array of sub-wavefront sampling elements.

14. The wavefront sensor of claim 13 where the first beam scanner is configured to track the eye so that only desired portion(s) of the wavefront from the eye is(are) always sampled even when the eye moves.

15. The wavefront sensor of claim 10, further comprising a wavefront compensator disposed at the first wavefront image plane, configured to partially or fully compensate one or more wavefront aberration component(s) so that the remaining wavefront aberration component(s) can be more precisely measured.

16. The wavefront sensor of claim 10 further comprising an eye image sensor configured to provide a live eye anterior image, and a second beam directing element configured to provide an optical path for eye imaging.

17. The wavefront sensor of claim 16 further comprising a display configured to display the live eye anterior image with an overlay of a qualitative and/or quantitative result of a wavefront measurement.

18. The wavefront sensor of claim 10 further comprising a second beam scanner, configured to track the eye by directing the light beam for generating the object wavefront to follow the eye.

19. The ophthalmic wavefront sensor of claim 10, further comprising:

a lens disposed between the array of sub-wavefront sampling elements and the array of position sensing devices, configured to relay and optically magnify the spacing between image spots formed by the array of sub-wavefront sampling elements at an image spot plane to the plane where the array of position sensing devices are disposed.

20. An ophthalmic wavefront sensor adapted to couple to an ophthalmic microscope, comprising:

a light source configured to receive a reference signal oscillating/pulsing at a reference frequency and to generate a beam of light formed by pulses of light at the reference frequency;

a first beam directing element configured to launch the beam of light from the light source into a patient eye and where a portion of the beam of light returned from the patient eye forms an object wavefront in the form of light pulses at the reference frequency;

an imaging sensor configured to provide a live eye anterior image;

a second beam directing element configured to provide an optical path for eye imaging;

an optical wavefront relay system, configured to relay an object wavefront from an object plane located at the anterior portion of a patient eye to a wavefront image plane along a beam path that can guide an incident wavefront relay beam having a large diopter range at the object plane to the wavefront image plane;

an array of high frequency response position sensing devices with each position sensing device configured to detect the amount of deflection of an image spot centroid from a reference position and to output a measurement signal indicating the amount of deflection;

an array of sub-wavefront sampling elements, disposed before the array of high frequency response position sensing devices and substantially at the wavefront image plane, with each sampling element in the array of sub-wavefront sampling elements configured to sample a sub-wavefront of the relayed wavefront and to focus a sampled sub-wavefront onto a corresponding high frequency response position sensing device in the array of high frequency response position sensing devices, where the sub-wavefront sampling elements are physically spaced from each other in such a way that each sampled sub-wavefront of a high diopter range object wavefront is focused only on the corresponding high frequency response position sensing device corresponding to the sub-wavefront sampling element; and an electronic frequency-sensitive detection system coupled to receive the reference signal and the measurement signal and coupled to the image sensor, with the electronic frequency-sensitive detection system configured to indicate only the magnitude of a frequency component of the measurement signal at about the reference frequency so that all noise signals, including 1/f noise, can be substantially suppressed, where f represents DC and frequencies lower than the reference frequency.

21. The ophthalmic wavefront sensor of claim 20 with the optical wavefront relay system including first and second lenses, each lens having a diameter, a focal length and an optical axis, with the optical wavefront relay system configured to relay the object wavefront from the object plane located at the anterior portion of the patient eye to a Fourier transfer plane located between the first and second lenses and to the wavefront image plane along the beam path where the focal lengths and diameters of the first and second lenses are selected to guide the incident wavefront relay beam having a large diopter range at the object plane to the wavefront image plane.

22. The ophthalmic wavefront sensor of claim 21, further comprising a second beam scanner disposed at the Fourier transform plane between the first and second lenses and configured to shift the relayed wavefront relative to the array of sub-wavefront sampling elements.

23. The ophthalmic wavefront sensor of claim 22, wherein the image sensor is further configured to provide information on the eye pupil location, and the second beam scanner is configured to track the eye by shifting the relayed wavefront relative to the array of sub-wavefront sampling elements such that the same portion(s) of the wavefront from the eye is(are) sampled even when the eye is moved.

24. The ophthalmic wavefront sensor of claim 20, further comprising a first beam scanner, configured to track the eye by directing the light beam for generating the object wavefront to follow the eye.

25. The ophthalmic wavefront sensor of claim 20, further comprising:
a lens disposed between the array of sub-wavefront sampling elements and the array of position sensing devices, configured to relay and optically magnify the spacing between image spots formed by the array of sub-wavefront sampling elements at an image spot plane to the plane where the array of position sensing devices are disposed.

26. An ophthalmic wavefront sensor adapted to couple to an ophthalmic microscope, comprising:
a light source configured to receive a reference signal oscillating/pulsing at a reference frequency and to generate a beam of light formed by pulses of light at the reference frequency;
a first beam directing element configured to launch the beam of light from the light source into a patient eye and where a portion of the beam of light returned from the patient eye forms an object wavefront in the form of light pulses at the reference frequency;
an imaging sensor configured to provide a live eye anterior image;
a second beam directing element configured to provide an optical path for eye imaging;
a first optical wavefront relay system, configured to relay an object wavefront from a first object plane located at the anterior portion of a patient eye to a first wavefront image plane along a first beam path that can guide an incident wavefront relay beam having a large diopter range at the object plane to the first wavefront image plane;
a second optical wavefront relay system having a second object plane located substantially at the first wavefront image plane, configured to further relay the object wavefront from the second object plane to a second wavefront image plane along a second beam path that can guide the incident wavefront relay beam having a large diopter range at the first object plane to the second wavefront image plane;
an array of high frequency response position sensing devices with each position sensing device configured to detect the amount of deflection of an image spot centroid from a reference position and to output a measurement signal indicating the amount of deflection;
an array of sub-wavefront sampling elements, disposed before the array of high frequency response position sensing devices and substantially at the second wavefront image plane, with each sampling element in the array of sub-wavefront sampling elements configured to sample a sub-wavefront of the relayed wavefront and to focus a sampled sub-wavefront onto a corresponding high frequency response position sensing device in the array of high frequency response position sensing devices, where the sub-wavefront sampling elements are physically spaced from each other in such a way that each sampled sub-wavefront of a high diopter range object wavefront is focused only on the corresponding high frequency response position sensing device corresponding to the sub-wavefront sampling element; and
an electronic frequency-sensitive detection system coupled to receive the reference signal and the measurement signal, with the electronic frequency-sensitive detection system configured to indicate only the magnitude of a frequency component of the measurement signal at about the reference frequency so that all noise signals, including 1/f noise, can be substantially suppressed, where f represents DC and frequencies lower than the reference frequency.

27. The ophthalmic wavefront sensor of claim 26 with the first optical wavefront relay system including first and second lenses, each lens having a diameter, a focal length and an optical axis, where the focal lengths and diameters of the first and second lenses are selected to guide the incident wavefront relay beam having a large diopter range at the first object plane to the first wavefront image plane; and
the second optical wavefront relay system including third and fourth lenses, each lens having a diameter, a focal length and an optical axis, where the focal lengths and diameters of the third and fourth lenses are selected to guide the incident wavefront relay beam having a large diopter range at the first object plane further to the second wavefront image plane.

28. The ophthalmic wavefront sensor of claim 27 with the third lens configured to guide the object wavefront to a Fourier transfer plane located between the third and fourth lenses.

29. The ophthalmic wavefront sensor of claim 28 further comprising a second beam scanner, disposed at the Fourier transform plane between the third and fourth lenses, configured to shift the relayed wavefront relative to the array of sub-wavefront sampling elements.

30. The ophthalmic wavefront sensor of claim 29, wherein the image sensor is further configured to provide information on the eye pupil location, and the second beam scanner is configured to track the eye by shifting the relayed wavefront relative to the array of sub-wavefront sampling elements such that the same portion(s) of the wavefront from the eye is(are) sampled even when the eye is moved.

31. The ophthalmic wavefront sensor of claim 26, further comprising a first beam scanner, configured to track the eye by directing the light beam for generating the object wavefront to follow the eye.

32. The ophthalmic wavefront sensor of claim 26, further comprising:
a lens disposed between the array of sub-wavefront sampling elements and the array of position sensing devices, configured to relay and optically magnify the spacing between image spots formed by the array of sub-wavefront sampling elements at an image spot plane to the plane where the array of position sensing devices are disposed.

33. An ophthalmic wavefront sensor comprising:
an optical wavefront relay system, configured to relay an object wavefront from an object plane located at the anterior portion of a patient eye to a wavefront image plane along a beam path that can guide an incident wavefront relay beam having a large diopter range at the object plane to the wavefront image plane;
a beam scanner/deflector disposed along the beam path, configured to fully intercept and scan the wavefront relay beam in two dimensions;
an array of position sensing devices with each position sensing device configured to detect the amount of two dimensional deflection of an image spot centroid from a reference position and to output a measurement signal indicating the amount of two dimensional deflection; and
an array of sub-wavefront sampling elements, disposed before the array of position sensing devices and substantially at the wavefront image plane, with each sampling element in the array of sub-wavefront sampling elements configured to sample a sub-wavefront of the relayed wavefront and to focus a sampled sub-wavefront onto a corresponding position sensing device in the array of position sensing devices, where the sub-wavefront sampling elements are physically spaced from each other in such a way that each sampled sub-wavefront of a high diopter range object wavefront is focused only on the corresponding position sensing device corresponding to the sub-wavefront sampling element.

34. The ophthalmic wavefront sensor of claim 33 with the optical wavefront relay system including first and second lenses, each lens having a diameter, a focal length and an optical axis, with the optical wavefront relay system configured to relay the object wavefront from the object plane located at the anterior portion of the patient eye to a Fourier transfer plane located between the first and second lenses and to the wavefront image plane along the beam path where the focal lengths and diameters of the first and second lenses are selected to guide the incident wavefront relay beam having a large diopter range at the object plane to the wavefront image plane, and with the beam scanner/deflector disposed substantially at the Fourier transfer plane located between the first and second lenses.

35. The ophthalmic wavefront sensor of claim 33, further comprising:
a lens disposed between the array of sub-wavefront sampling elements and the array of position sensing devices, configured to relay and optically magnify the spacing between image spots formed by the array of sub-wavefront sampling elements at an image spot plane to the plane where the array of position sensing devices are disposed.

36. An ophthalmic wavefront sensor comprising:
a first optical wavefront relay system, configured to relay an object wavefront from a first object plane located at the anterior portion of a patient eye to a first wavefront image plane along a first beam path that can guide an incident wavefront relay beam having a large diopter range at the first object plane to the first wavefront image plane;
a second optical wavefront relay system having a second object plane located substantially at the first wavefront image plane, configured to further relay the object wavefront from the second object plane to a Fourier transform plane and to a second wavefront image plane along a second beam path that can guide the incident wavefront relay beam having a large diopter range at the first object plane to the second wavefront image plane;
a beam scanner/deflector disposed substantially at the Fourier transform plane, configured to fully intercept and scan the wavefront relay beam;
an array of position sensing devices with each position sensing device configured to detect the amount of deflection of an image spot centroid from a reference position and to output a measurement signal indicating the amount of deflection; and
an array of sub-wavefront sampling elements, disposed before the array of position sensing devices and substantially at the second wavefront image plane, with each sampling element in the array of sub-wavefront sampling elements configured to sample a sub-wavefront of the relayed wavefront and to focus a sampled sub-wavefront onto a corresponding position sensing device in the array of position sensing devices, where the sub-wavefront sampling elements are physically spaced from each other in such a way that each sampled sub-wavefront of a high diopter range object wavefront is focused only on the corresponding position sensing device corresponding to the sub-wavefront sampling element.

37. The ophthalmic wavefront sensor of claim 36 with the first optical wavefront relay system including first and second lenses, each lens having a diameter, a focal length and an optical axis, where the focal lengths and diameters of the first and second lenses are selected to guide the incident wavefront relay beam having a large diopter range at the first object plane to the first wavefront image plane; and
the second optical wavefront relay system including third and fourth lenses, each lens having a diameter, a focal length and an optical axis, where the focal lengths and diameters of the third and fourth lenses are selected to further guide the incident wavefront relay beam having a large diopter range at the first object plane to the second wavefront image plane.

38. The ophthalmic wavefront sensor of claim 36, further comprising:
a lens disposed between the array of sub-wavefront sampling elements and the array of position sensing devices, configured to relay and optically magnify the spacing between image spots formed by the array of sub-wavefront sampling elements at an image spot plane to the plane where the array of position sensing devices are disposed.

39. An ophthalmic wavefront sensor comprising:
a light source configured to receive a reference signal oscillating/pulsing at a reference frequency and to generate a beam of light formed by pulses of light at the reference frequency;
a beam directing element configured to launch the beam of light from the light source into a patient eye and where a portion of the beam of light returned from the patient eye forms an object wavefront in the form of light pulses at the reference frequency;
an optical wavefront relay system, configured to relay an object wavefront from an object plane located at the anterior portion of a patient eye to a wavefront image plane along a beam path that can guide an incident wavefront relay beam having a large diopter range at the object plane to the wavefront image plane;

an array of high frequency response position sensing devices with each position sensing device configured to detect the amount of deflection of an image spot centroid from a reference position and to output a measurement signal indicating the amount of deflection; and an array of sub-wavefront sampling elements, disposed before the array of high frequency response position sensing devices and substantially at the wavefront image plane, with each sampling element in the array of sub-wavefront sampling elements configured to sample a sub-wavefront of the relayed wavefront and to focus a sampled sub-wavefront onto a corresponding high frequency response position sensing device in the array of high frequency response position sensing devices, where the sub-wavefront sampling elements are physically spaced from each other in such a way that each sampled sub-wavefront of a high diopter range object wavefront is focused only on the corresponding high frequency response position sensing device corresponding to the sub-wavefront sampling element.

40. The ophthalmic wavefront sensor of claim 39 with the optical wavefront relay system including first and second lenses, each lens having a diameter, a focal length and an optical axis, where the focal lengths and diameters of the first and second lenses are selected to guide the wavefront relay beam having a large diopter range at the object plane to the wavefront image plane.

41. The ophthalmic wavefront sensor of claim 39, further comprising: a lens disposed between the array of sub-wavefront sampling elements and the array of high frequency response position sensing devices, configured to relay and optically magnify the spacing between image spots formed by the array of sub-wavefront sampling elements at an image spot plane to the plane where the array of position sensing devices are disposed.

* * * * *

UNITED STATES PATENT AND TRADEMARK OFFICE
CERTIFICATE OF CORRECTION

Page 1 of 1

PATENT NO. : 8,777,413 B2
APPLICATION NO. : 13/459914
DATED : July 15, 2014
INVENTOR(S) : Yan Zhou et al.

It is certified that error appears in the above-identified patent and that said Letters Patent is hereby corrected as shown below:

In the Claims

Column 26, lines 8-9, "Fourier transfer plane", should read --Fourier transform plane--

Column 27, lines 51-52, "Fourier transfer plane", should read --Fourier transform plane--

Column 29, lines 10-11, "Fourier transfer plane", should read --Fourier transform plane--

Column 30, lines 50-51, "Fourier transfer plane", should read --Fourier transform plane--

Column 31, lines 45-46 and line 52, "Fourier transfer plane", should read --Fourier transform plane--

Signed and Sealed this
Seventeenth Day of March, 2015

Michelle K. Lee
*Director of the United States Patent and Trademark Office*